(12) United States Patent
Lemay

(10) Patent No.: US 11,249,148 B2
(45) Date of Patent: Feb. 15, 2022

(54) MAGNETIC FLUX PICKUP AND ELECTRONIC DEVICE FOR SENSING MAGNETIC FIELDS

(71) Applicant: QUINC.TECH INC., San Diego, CA (US)

(72) Inventor: Lee Lemay, San Diego, CA (US)

( * ) Notice: Subject to any disclaimer, the term of this patent is extended or adjusted under 35 U.S.C. 154(b) by 137 days.

(21) Appl. No.: 16/582,711

(22) Filed: Sep. 25, 2019

(65) Prior Publication Data

US 2020/0018803 A1   Jan. 16, 2020

Related U.S. Application Data

(63) Continuation-in-part of application No. 16/367,230, filed on Mar. 27, 2019.

(60) Provisional application No. 62/648,547, filed on Mar. 27, 2018.

(51) Int. Cl.
| | | |
|---|---|---|
| *G01R 33/00* | (2006.01) | |
| *G01R 33/035* | (2006.01) | |
| *H01F 6/06* | (2006.01) | |
| *G01R 33/025* | (2006.01) | |
| *A61B 5/0522* | (2021.01) | |
| *G01V 3/08* | (2006.01) | |
| *A61B 5/245* | (2021.01) | |

(52) U.S. Cl.
CPC ........ *G01R 33/0356* (2013.01); *A61B 5/0522* (2013.01); *G01R 33/025* (2013.01); *H01F 6/06* (2013.01); *A61B 5/245* (2021.01); *G01V 3/08* (2013.01)

(58) Field of Classification Search
CPC ............... G01R 33/00; G01R 33/0035; G01R 33/0023; G01R 33/0017; G01R 31/3191; G01R 33/025; G01R 33/0358; G01R 33/0356; G01B 7/004; G01C 17/38; G06F 3/017; G06F 3/0346; G06F 3/012; H01L 39/223; H01F 6/06; A61B 5/0522; A61B 5/245; G01V 3/08
See application file for complete search history.

(56) References Cited

U.S. PATENT DOCUMENTS

| | | | | |
|---|---|---|---|---|
| 5,283,523 A | * | 2/1994 | Uhl | ..................... G01R 33/0358 324/225 |
| 2012/0088674 A1 | * | 4/2012 | Faley | ....................... H01C 1/14 505/162 |
| 2018/0151792 A1 | * | 5/2018 | Selvamanickam | ... H01L 39/126 |

* cited by examiner

*Primary Examiner* — Patrick Assouad
*Assistant Examiner* — Taqi R Nasir
(74) *Attorney, Agent, or Firm* — Enrique A. Monteagudo, Esq.

(57) ABSTRACT

Aspects of the present disclosure generally pertain to a magnetic field sensor with flex coupling structures. Aspects of the present disclosure are more specifically directed toward Nanoscale Superconducting Quantum Interference Devices (nanoSQUIDs) with very low white flux noise characteristics can be fashioned into very sensitive magnetic field sensors by using external structures to increase the amount of flux that passes through the nanoSQUID aperture. Aspects of the present disclosure are also directed toward a magnetic flux pickup that can be coupled to a SQUID or nanoSQUID and incorporates an input coil made of a superconducting tape, which may be embodied in an electronic device for sensing magnetic fields, or more specifically an application specific electronic device for sensing a sensed property such as for geophysical sensing or biomedical imaging.

11 Claims, 13 Drawing Sheets

MAGNETIC FLUX PICKUP AND ELECTRONIC DEVICE FOR SENSING MAGNETIC FIELDS

CROSS-REFERENCE TO RELATED APPLICATIONS

This application is a continuation in part of U.S. patent application Ser. No. 16/367,230, filed Mar. 27, 2019 and entitled Electronic Device For Sensing Magnetic Fields; which claims priority to U.S. provisional patent application 62/648,547, filed Mar. 27, 2018 and entitled Magnetic Field Sensor with Flux Coupling Structures, the contents of which are incorporated herein by reference in its entirety.

STATEMENT OF FEDERALLY SPONSORED RESEARCH OR DEVELOPMENT

This invention was made with government support under HR001118C0046 awarded by Defense Advanced Research Projects Agency (DARPA). The government has certain rights in the invention.

BACKGROUND OF THE INVENTION

Technical Field

The present disclosure generally pertains to mechanisms and methods for improving signal detection and amplification, and is more particularly directed towards mechanisms and methods for measuring magnetic fields with high sensitivity.

Related Art

The ability to measure magnetic fields with high sensitivity is an enabler for biomedical imaging and geophysical exploration. Low temperature superconductors operating at 4 degrees Kelvin can be fashioned into SQUIDs with sensitivities that are better than 1 femtoTesla/Hz$^{1/2}$. This level of sensitivity allows direct measurement of neural and muscular activity, which has enabled Magnetoencephalography (MEG) and other biomedical imaging. However, low temperature systems are expensive, and usually rely on liquid Helium, a finite resource which is expensive and may run out. Furthermore, low temperature superconductors require bulky insulating cryogenic systems, which mean that the SQUID sensor cannot be placed directly next to the subject. This standoff distance attenuates the signals that are being measured.

To overcome the expense, reliance on liquid Helium, bulky cryogenic apparatus, and to decrease the standoff distance, it is desirable to develop an equally sensitive SQUID from high temperature superconductors operating at up to 77 degrees Kelvin. However, high temperature SQUIDs have traditionally been orders of magnitude less sensitive than low temperature SQUIDs. This is due to material properties and higher temperatures that introduce a higher amount of white flux noise into their operation. Furthermore, lack of maturity in processing the high temperature superconducting materials have made it difficult to fabricate multi-layer structures out of the high temperature superconductor, which in turn has made it difficult to develop efficient multi-turn flux focusing coils.

In addition, current high temperature SQUIDs are made on the order of micrometers, which have inductance that contributes to the higher noise floor present in high temperature superconducting SQUIDs. For example, U.S. Pat. No. 5,767,043 to Cantor, et al. on Jun. 16, 1998, pertains to a multiple squid direct signal injection device formed on a single layer substrate. In particular, a low-noise directly coupled 10 micrometer gap dc SQUID magnetometer is disclosed. The magnetometer provides for single layer fabrication and is particularly applicable to high-T.sub.c superconductors operating at 77 Kelvin. A pair of dc SQUIDs are connected and biased in series such that the output voltage modulation with applied flux of the dual SQUID magnetometer, is double that of a single SQUID magnetometer. The bias current is applied to one SQUID and removed from the second SQUID of the pair. The magnetometer pick-up coil is directly coupled to the SQUID pair, providing for coherent modulation of the series-connected SQUIDS and a reduction of flux density noise of the device by a factor of 1/.sqroot.2.

Additional approaches have not resolved the above deficiencies identified by the inventor. For example, U.S. Pat. No. 6,690,162 to Schopohl, et al. on Feb. 10, 2004, pertains to a device for high-resolution measurement of magnetic fields. In particular, a device was proposed for high-resolution measurement, in particular for high-resolution absolute measurement of magnetic fields, having a network (1) of transitions (3) between superconductors (5, 6) which exhibit Josephson effects, called junctions below, the network comprising closed meshes (7, 8, 9, 10, 11, 12, 13), denoted by cells below, which in each case have junctions (3), which junctions are connected in a superconducting fashion, and at least three of these cells being connected in a superconducting and/or nonsuperconducting fashion. The object of that disclosure consists in further developing that device in such a way that it is possible to make absolute measurements of magnetic fields in a highly sensitive fashion. This object was achieved by virtue of the fact that the junctions (3) of the at least three cells (7, 8, 9) can be energized in such a way that a time-variant voltage drops in each case across at least two junctions of a cell, the time average of which voltage does not vanish, and in that the at least three cells were configured differently geometrically in such a way that the magnetic fluxes enclosed by the cells in the case of an existing magnetic field differ from one another in such a way that the frequency spectrum of the voltage response function has no significant .PHI..sub.0-periodic component with reference to the magnetic flux.

Separately, an ultra-thin film High Temperature Superconductor (HTS) tape with a bend diameter D of under 1 millimeter has very recently been demonstrated that has a reduced thickness, allowing for tighter winding and increased current (i.e., increased engineering current density). The HTS tape has been fabricated by removing a portion of the tape's substrate, so that the HTS portion is in the neutral axis of the tape. By reducing the substrate thickness, and carefully engineering the thickness of the different layers of the tape so that each component's Young's modulus is matched, the tape can be made to be flexible without degradation of its performance. Furthermore, reducing the substrate thickness results in a thinner tape, which may have a thickness of 15-30 μm. For example, U.S Pat. App. Pub. No. 2018/0151792 by Selvamanickam, published on May 31, 2018, pertains to such Ultra-Thin Film Superconducting Tapes, having embodiments directed to a superconducting tape being fabricated by processes which include removing a portion of the superconducting tape's substrate subsequent the substrate's initial formation, whereby a thickness of the superconducting tape is reduced to 15-80.mu.m.

The present disclosure is directed toward overcoming known problems and problems discovered by the inventor.

SUMMARY OF THE INVENTION

Aspects of the present disclosure generally pertain to a magnetic field sensor with flux coupling structures. Aspects of the present disclosure more specifically are directed toward a magnetic flux pickup that can be coupled to a SQUID or nanoSQUID and incorporates an input coil made of a superconducting tape.

A magnetic flux pickup for an electronic device for sensing magnetic fields is disclosed herein. The magnetic flux pickup includes a magnetic flux pickup loop electronically coupled to an input coil. The magnetic flux pickup loop has a pickup loop center axis, the magnetic flux pickup loop includes a first pickup end, a second pickup end, and an open loop, the open loop extending between the first pickup end and the second pickup end and circumscribes at least 350 degrees about the pickup loop center axis, the pickup loop is made of a first superconducting material, the open loop is characterized by a loop diameter defined as an average diametrical distance between opposing sides of the open loop. The input coil has an input coil center axis, the input coil includes a first coil terminal end and a second coil terminal end, and a coil of at least one loop, the coil extends between the first coil terminal end and the second coil terminal end and circumscribes at least 350 degrees about the input coil center axis, the input coil made of a superconducting tape having a tape width and tape thickness, the input coil is characterized by a coil diameter defined as an average diametrical distance between opposing sides of the coil, the first terminal coil end electrically coupled to the first pickup end of the magnetic flux pickup loop, the second coil terminal end electrically coupled to the second pickup end of the magnetic flux pickup loop.

According to one embodiment, an electronic device for sensing magnetic fields is disclosed herein. The electronic device includes a first electronic device terminal, a second electronic device terminal, a first Superconducting Quantum Interference Device (SQUID), a SQUID coupling loop, and the abovementioned magnetic flux pickup. The first SQUID includes a first superconducting trace extending between two first opposing ends, a second superconducting trace extending between two second opposing ends, and a first pair of Josephson Junctions electrically coupled in parallel between each of the first superconducting trace and the second superconducting trace at the first opposing ends and second opposing ends of the first superconducting trace and the second superconducting trace, respectively, the first SQUID is electrically coupled in series between the first terminal via the first superconducting trace, and the second terminal via the second superconducting trace. The SQUID coupling loop is made of a first superconducting material shaped into a closed loop about a coupling center axis, the SQUID coupling loop characterized by a coupling loop diameter defined as an average diametrical distance between opposing sides of the closed loop, the SQUID coupling loop integrated with the second superconducting trace such that the second superconducting trace forms a first segment of the superconducting loop, the SQUID coupling loop electrically coupled in series between the first terminal via the second superconducting trace and the second terminal.

According to another embodiment, an application specific electronic device for sensing a sensed property is disclosed herein. The application specific electronic device includes the abovementioned electronic device for sensing magnetic fields, a cryogenic system configured to cool the SQUID below its critical temperature, a means to reduce magnetic fields from secondary sources, an application specific signal processor configured to read and interpret voltages between the first terminal and the second terminal as a magnetic field strength, a data processor and user interface configured to interpret the magnetic field strength according to the sensed property, and to the communicate the sensed property to a user.

DETAILED DESCRIPTION

Figure 1:
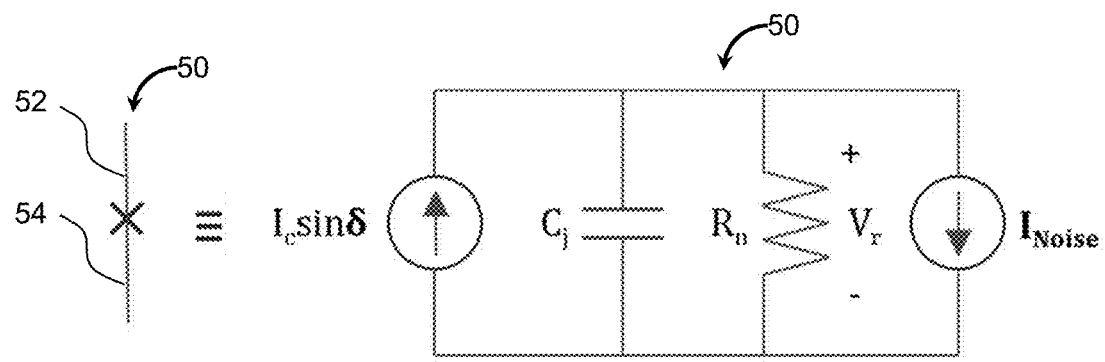
FIG. 1 schematically illustrates the RCSJ model with current noise for a Josephson Junction (JJ).

Aspects of the present disclosure generally pertain to a magnetic field sensor with flux coupling structures. Generally, Nanoscale Superconducting Quantum Interference Devices (nanoSQUIDs) with very low white flux noise characteristics can be fashioned into very sensitive magnetic field sensors by using external structures to increase the amount of flux that passes through the nanoSQUID aperture. One such structure is a superconducting coupling loop that shares part of a circuit with the nanoSQUID, and couples flux into the nanoSQUID primarily through kinetic inductance rather than geometric inductance. Another structure is a magnetic flux pickup that can be coupled to a SQUID or nanoSQUID.

The present disclosure is intended to address a problem that arises when a system is measuring a magnetic signal but the system does not have sufficient sensitivity to resolve the signal. This may occur in geophysical sensing, when magnetic signals that are scattering from structures below the surface of the earth are measured to determine information about the composition and geometry of the structures. It may also occur in biomedical imaging, when magnetic signals generated by biological structures are measured to determine information about the biological structures. Examples of this are magnetoencephalography, which measures magnetic fields generated by neurons, and magnetocardiography, which measures magnetic signals generated by the heart. Another example is Magnetic Resonance Imaging (MRI), which forms pictures of the body using measurements of the magnetic field that are generated by hydrogen atoms in the body.

In embodiments, the geometry of the nanoSQUID and coupling loop can be optimized to maximize the coupling of flux into the nanoSQUID via kinetic inductance. The amount of flux that passes through the coupling loop can be increased using secondary flux focusing structures such as Lenz lenses or pickup coils. The Lenz lens can also shield flux from entering parts of the circuit where flux is undesirable. The Lenz lens may also be integrated into a feedback loop to linearize the system's voltage output. To increase the sensitivity and voltage response of the device, multiple nanoSQUIDs may be patterned on the edge of the coupling loop in a series or parallel configuration. The devices described in this patent may be used in a SQUID cascade, which utilizes two or more independent devices with different sensitivities to achieve an extended dynamic range.

Further, the present disclosure addresses several of the above identified problems while mitigating additional system cost and additional complexity. Thus, this disclosure may be useful for providing an improved mechanisms and methods for measuring magnetic fields with high sensitivity Various aspects of the novel systems, devices, and methods are described more fully hereinafter with reference to the accompanying drawings. The detailed description set forth below in connection with the appended drawings is intended as a description of various configurations and embodiments, and is not intended to represent the only configurations in which the concepts described herein may be practiced. The detailed description includes specific details for the purpose of providing a thorough understanding of various concepts. In particular, it will be apparent to those skilled in the art that these concepts may be practiced without these specific details. In some instances, well known structures and components are shown in block diagram form in order to avoid obscuring such concepts.

FIG. 1 schematically illustrates the RCSJ model with current noise for a Josephson Junction (JJ) 50. The JJ, denoted by an 'x' intersecting a line, is on the left, and the RCSJ model is on the right. It is generally understood that the JJ joins one side (junction end 52) to an other side (junction end 54). As illustrated, the quantity δ is the gauge invariant phase difference across the junction.

Figure 2:
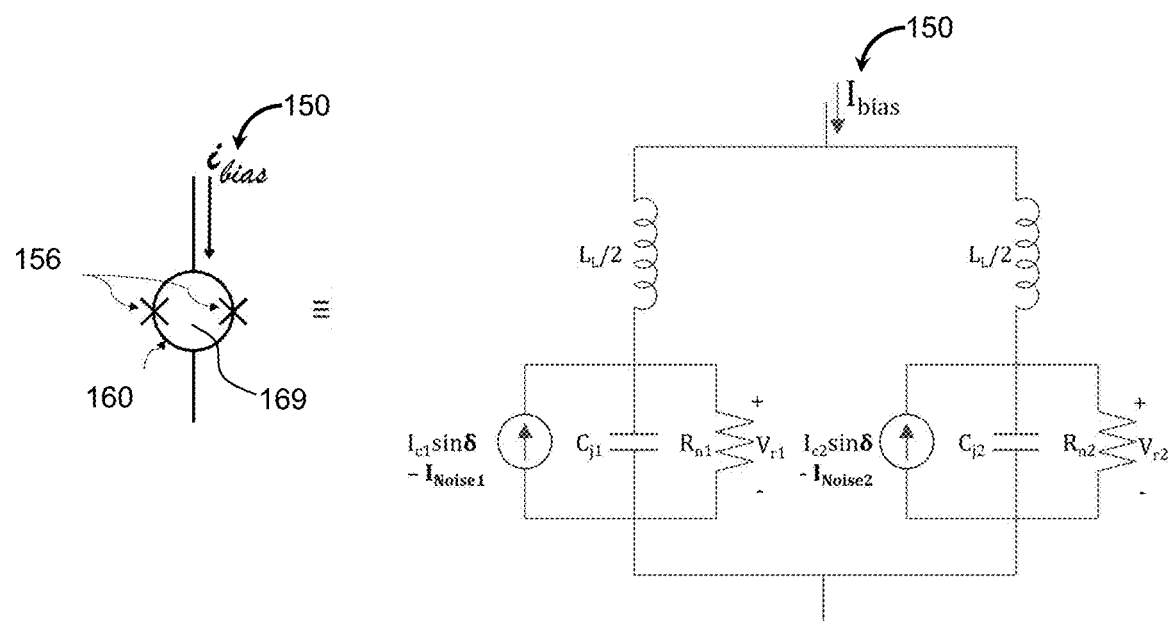
FIG. 2 schematically illustrates a DC SQUID approximated using the RCSJ model of FIG. 1.

FIG. 2 schematically illustrates a DC SQUID approximated using the RCSJ model of FIG. 1. The DC SQUID (SQUID 150) is denoted as a loop (superconducting SQUID loop 160) with two Josephson Junctions (pair of JJs 156), shown on the left. The circuit schematic for the SQUID 150 using the RCSJ model is shown on the right.

SQUIDs are non-linear devices that can be used, for example, to sense magnetic fields, or to divide the signal in a system into distinct channels, where each channel contains information about a different portion of the dynamic range of the signal. A DC SQUID is made from a superconducting loop that contains two Josephson Junctions (JJs). A JJ is a very thin break in the superconductor that allows a slight overlap in the electron pair wave functions between the two sides of the break.

The SQUID 150 may generally be made from a superconducting SQUID loop 160 containing at least one pair of JJs 156. The symbol for the JJ and the Resistively Capacitively Shunted Junction (RCSJ) model are shown in FIG. 1. The RCSJ model approximates the Josephson Junction as a current source shunted by a capacitor and a resistor. The current is sinusoidal as a function of the gauge invariant phase difference of the superconducting wave function across the junction. A current noise source is included here, although it is not always present in the RCSJ model.

As indicated by the electrical symbol, a superconducting SQUID loop may symmetrically couple the JJs. However, as discussed below, the superconducting SQUID loop 160 may asymmetrically (in at least one axis) couple the pair of JJs 156

As discussed below, one or more SQUIDs 150 may be incorporated into an electronic device 100 (FIG. 4) for sensing magnetic fields. Further, it is understood, that said electronic device 100 may include additional components (e.g., nanoSQUID electronics 200 FIG. 10) associated with the operation, use, and/or application of the electronic device 100, and particularly the SQUID 150. Moreover, any additional components including but not limited to the nanoSQUID electronics 200 may be electronically coupled via any appropriate means (e.g., wired, wirelessly, etc.).

To operate properly, the one or more SQUIDs 150 need to be cooled down below its critical temperature (i.e., the temperature at which its elements become superconducting). The cryogenic equipment (not shown) to cool the SQUID 150 down may consist of a cryocooler or a cryostat with a cooling mechanism, insulation system, and control system or the like.

Similarly, the SQUIDs 150 need to be shielded from magnetic fields that are not from the signal of interest. This can be done by placing a superconducting magnetic shield over them, or by configuring each SQUID 150 as a gradiometer. A gradiometer SQUID cancels out any common mode signal, and could be configured to be sensitive to the magnetic field produced by the signal of interest.

As illustrated, the inductance $L_L$ is the inductance of the superconducting SQUID loop 160, which is made up of both geometric and kinetic inductances. To overcome the higher noise floor present in high temperature superconducting SQUIDs, the SQUID 150 may be fashioned with extremely low inductance. When the inductance in the SQUID 150 is decreased, a given flux will induce a larger screening current in the device, thereby increasing the signal that is measured. Here, decreasing the inductance of the SQUID 150 may be accomplished by decreasing its size. In particular, the SQUID may be a "nanoSQUID", whose length, width, or both are measured in tens or hundreds of nanometers. For example, at least one dimension may be 999 nanometers or less.

Those skilled in the art will be familiar with SQUIDs in general, and will recognize "length" and "width" as corresponding to general dimensions of an aperture 169 formed by the superconducting SQUID loop 160 electrically coupling a pair of JJs, for example. The shape of the superconducting SQUID loop 160 may curved, rectilinear, or a combination thereof. According to one embodiment, and as discussed below, the superconducting SQUID loop 160 may be formed by a superconducting trace fixed to a substrate, electrically coupling each pair of junction ends 52, 54 (FIG. 1).

As a "nanoSQUID", the SQUID 150 may advantageously achieve very low inductance and very low white flux noise levels, much lower than traditional SQUIDs. Like a regular Direct Current (DC) SQUID, here the SQUID 150 is still composed of a superconducting loop (superconducting SQUID loop 160) with two JJs (pair of JJs 156).

Unlike traditional SQUIDS, here, the superconducting SQUID loop 160 in the center of the SQUID (aperture 169) is tens to hundreds of nanometers wide, and can be tens of nanometers to several microns long, having an exaggerated oblong or rectangular shape. The center of the loop, which is not superconducting, may be fashioned by removing the superconducting material, or by processing it to remove its superconductivity.

Figure 3:
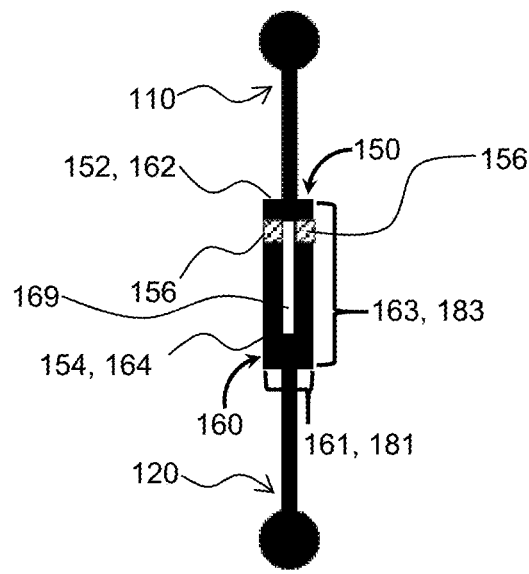
FIG. 3 shows a nanoSQUID, according to an exemplary embodiment of the present disclosure.

FIG. 3 shows a nanoSQUID, according to an exemplary embodiment of the present disclosure. As discussed above, the SQUID 150 may have an elongated or otherwise asymmetric shape in at least one axis. As illustrated, the SQUID 150 shows a possible geometry for a nanoSQUID for use in the electronic device 100 (FIG. 4) for sensing magnetic fields. As above, the SQUID 150 may include the superconducting SQUID loop 160 and the pair of Josephson Junctions (JJs) 156. As above, each JJ is substantially a very thin break in the superconducting SQUID loop 160, however, the pair of JJs 156 are shown exaggerated in size for ease of illustration.

According to one embodiment, and as shown, the superconducting SQUID loop 160 may include a first superconducting trace 152 and a second superconducting trace 154 joined at the pair of JJs 156. In particular, the pair of Josephson Junctions 156 are electrically coupled in parallel between the first superconducting trace 152 and the second superconducting trace 154. The SQUID 150 may be electrically coupled in series between a first terminal 110 via the first superconducting trace 152, and a second terminal 120 via the second superconducting trace 154.

For reference, the first superconducting trace 152 has a first trace length 162 as measured between one junction end 52 (FIG. 1) of each of the first pair of JJs 156, and the second superconducting trace 154 has a second trace length 164 as measured between the other junction end 54 (FIG. 1) of each of the first pair of JJs 156.

Further and as above, the superconducting SQUID loop 160 forms the aperture 169, which has Josephson Junction width 161 and a Josephson Junction depth 163. In this exemplary embodiment, the JJ width 161 is understood as corresponding to the physical distance between the pair of JJs 156, and the JJ depth 163 as corresponding to the physical distance perpendicularly (i.e., relative to the width) away from the pair of JJs 156. For example, and as shown, here the aperture 169 is formed by the first superconducting trace 152 directly extending linearly between one junction end 52 of each of the pair of JJs 156, and the second superconducting trace 154 extending rectangularly between the other junction end 54 of each of the pair of JJs 156 (here, linearly departing one JJ 156, turning perpendicularly toward the other JJ 156, and then returning linearly to the other JJ 156.

According to one embodiment, the first superconducting trace 152 linearly couples the one junction ends 52 of each of the pair of Josephson Junctions 156, such that the first superconducting trace 152 defines the Josephson Junction width 161 and is substantially the same as first trace length 162. Further, the second superconducting trace 154 rectilinearly couples the other junction ends 54 of each of the first pair of Josephson Junctions 156, such that the second superconducting trace 154 defines the Josephson Junction insertion depth 163 (measured perpendicularly from the first superconducting trace 152) and the second trace length 164 is substantially the sum of the Josephson Junction width 161 and twice the Josephson Junction insertion depth 163.

According to one embodiment, the second trace length 164 may be substantially longer than the first trace length 162. For example, the second trace length 164 may be at least twice the first trace length 162. Also for example, the second trace length 164 may be at least seven times the first trace length 162. Also for example, the second trace length 164 may be at least twice twenty-five times the first trace length 162.

As above, the SQUID may be a "nanoSQUID", whose length, width, or both are measured in tens or hundreds of nanometers. According to one embodiment, the first trace length 162 may be less than 999 nm. According to another embodiment, the first trace length 162 may be 200 nm±50%, and the second trace length 162 may be 5000 nm±50%. Preferably, the first trace length 162 may be 200 nm±10%; and the second trace length 162 may be 5000 nm±10%.

Figure 4:
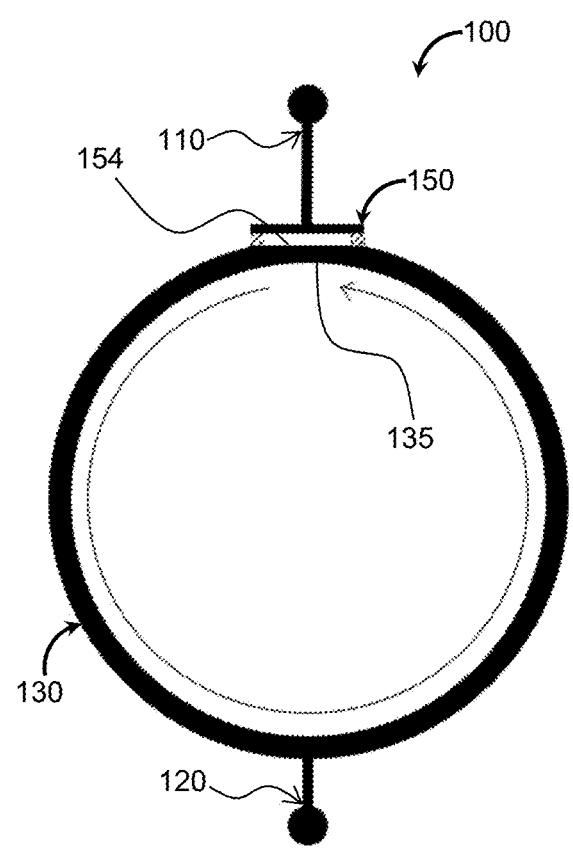
FIG. 4 shows a nanoSQUID oriented tangentially to a superconducting coupling loop.
Figure 5:
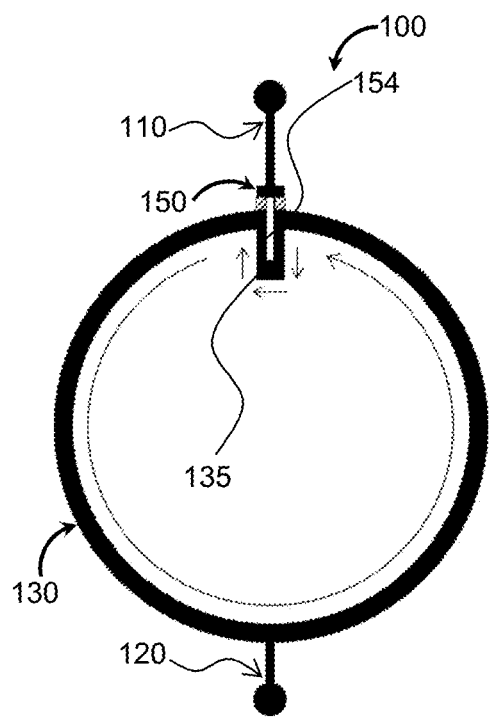
FIG. 5 shows a nanoSQUID oriented perpendicularly to a superconducting coupling loop, according to an exemplary embodiment of the present disclosure.

FIG. 4 shows a nanoSQUID oriented "tangentially" (i.e., JJ width>JJ depth) to a superconducting coupling loop. As above, one or more SQUIDs 150 may be incorporated into the electronic device 100 for sensing magnetic fields. Further, it is understood, that said electronic device 100 may include additional components (e.g., nanoSQUID electronics 200 FIG. 10) associated with the operation, use, and/or application of the electronic device 100, and particularly the SQUID 150. As shown, the electronic device 100 may include the first terminal 110, the second terminal 120, a superconducting coupling loop 130, and one or more SQUIDs 150 electrically coupled in series between the first terminal 110 and the second terminal 120. In particular, one or more SQUIDs 150 may be electrically coupled in series to the second terminal 120 via the superconducting coupling loop 130 (as shown), and/or electrically coupled in series to the first terminal 110 and via the superconducting coupling loop 130 (FIG. 5).

In the past nanoSQUIDs have been manufactured from Yttrium Barium Copper Oxides (YBCO), a high temperature superconductor, with similar white flux noise levels as low temperature SQUIDs. However, the sensitivity of the low temperature SQUIDs still exceeds the sensitivity of the high temperature nanoSQUIDs, because the nanoSQUIDs are very small and very little flux will enter the nanoSQUIDs' aperture.

To address this, SQUID 150 may be fabricated on the edge of the superconducting coupling loop 130. The superconducting coupling loop 130 may then directly couple flux into the SQUID 150. According to one embodiment, a long edge of the SQUID 150 may be coupled "tangentially" to an edge of the loop superconducting coupling loop 130 (e.g., the second superconducting trace 154 forming a segment 135 of the superconducting coupling loop 130).

By directly coupling flux of the superconducting coupling loop 130 into the SQUID 150, an "effective area" of the nanoSQUID (SQUID 150.) can be increased.

The increase in the effective area of the nanoSQUID can be analytically approximated according to the general equation:

(1) Effective Area=(nanoSQUID Area)+(Coupling Inductance)/(Loop Inductance)*Loop Area Further, the coupling inductance can be approximated as:

(2) Coupling Inductance=(nanoSQUID Geometric Inductance)/2+nanoSQUID Kinetic Inductance, where the geometric inductance is that of a slit (aperture 169):

(3) nanoSQUID Geometric Inductance≅0.3 pH/µm, and the kinetic inductance comes from the shared edge of the nanoSQUID and the coupling loop:

(4) nanoSQUID Kinetic Inductance/µm=(µ_0λ_L)/w coth (t/λ_L)

where µ_0 is the magnetic permeability, λ_L is the London penetration depth, w is the width of the shared edge between the nanoSQUID and the coupling loop, and t is the thickness of the superconducting film.

For a London penetration depth of 400 nm, film thickness of 30 nm, and trace width of 2 um, the kinetic inductance is 3.4 pH/µm, over 11 times that of the geometric inductance per unit length. A London penetration depth of 400 nm is higher than is usual for typical YBCO devices but provides a better match to experimental data.

Even using this configuration of nanoSQUID fashioned on the edge of a coupling loop, oriented tangentially, high temperature superconducting SQUIDs might not achieve the same magnetic field sensitivity as low temperature SQUIDs.

FIG. 5 shows a nanoSQUID oriented "perpendicularly" (i.e., JJ width<JJ depth) to a superconducting coupling loop, according to an exemplary embodiment of the present disclosure. As above, the electronic device 100 may include the first terminal 110, the second terminal 120, the superconducting coupling loop 130, and one or more SQUIDs 150. Also, as above the second superconducting trace 154 may form a segment 135 of the superconducting coupling loop 130.

In this preferred embodiment, one or more SQUIDs 150 of the electronic device 100 may still be made from high temperature superconductor, yet may equal or exceed the sensitivities of low temperature SQUIDs. Advantageously, the potentially much greater performance may allow the electronic device 100 to be used as a magnetometer, in an analog gradiometer, or in a software defined gradiometer that performs gradiometry by subtracting signals from two different sensors.

In this preferred embodiment, the electronic device 100 features a more efficient coupling of flux from the superconducting coupling loop 130 into the SQUID 150. This is achieved by "rotating" the nanoSQUID (SQUID 150) approximately 90 degrees, so that it is oriented perpendicularly to the superconducting coupling loop 130 or "dipping into" the aperture of the superconducting coupling loop 130.

The inventor has discovered, by "rotating" or orienting the SQUID 150 to be perpendicular rather than tangential to the coupling loop, it may significantly improve the performance of the SQUID 150, as it allows the same coupling inductance to be achieved as the tangentially oriented SQUID 150, but with a lower total inductance for the electronic device 100. Here, it can be seen that, for nanoSQUIDs of the same aperture size, the edge that is shared between the perpendicular nanoSQUID and the coupling loop is longer than the edge that is shared between the tangential nanoSQUID and coupling loop. This longer edge will increase the kinetic inductance of the perpendicularly oriented nanoSQUID, all of which, will contribute to the coupling inductance.

This in turn may allow the overall length of the perpendicularly oriented nanoSQUID to be decreased while still achieving the same amount of coupling as the tangentially oriented nanoSQUID. Decreasing the length (e.g., first trace length 162 plus second trace length 164) decreases the geometric inductance. As calculated above, because only half of the geometric inductance contributes to the coupling inductance, the overall inductance of the device is decreased while the coupling inductance stays the same. Thus, using a perpendicularly oriented nanoSQUID increases the sensitivity of the device.

Figure 6:
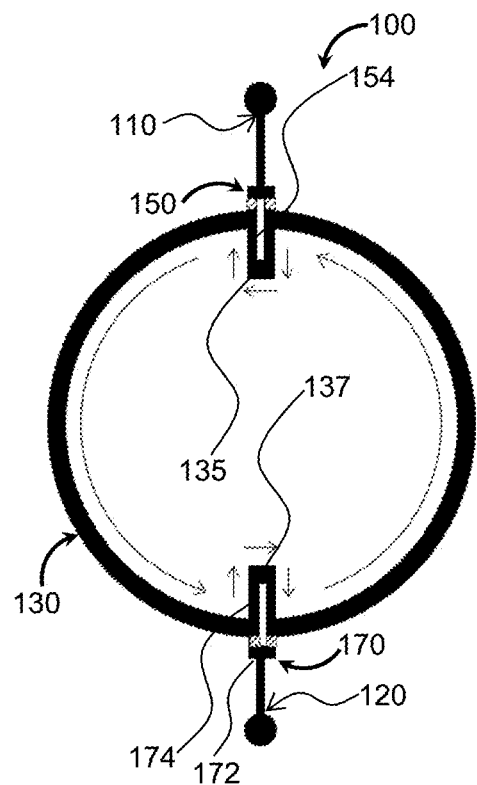
FIG. 6 shows two nanoSQUIDs connected to the same superconducting coupling loop, arranged in a series circuit, according to an exemplary embodiment of the present disclosure.

FIG. 6 shows two nanoSQUIDs connected to the same superconducting coupling loop, arranged in a series circuit, according to an exemplary embodiment of the present disclosure. In particular, two SQUIDs 150, 170 are electrically arranged in series, and both connected to the superconducting coupling loop 130.

As above, the electronic device 100 may include the first terminal 110, the second terminal 120, the superconducting coupling loop 130, and one or more SQUIDs 150, 170. Also, as above the second superconducting trace 154 may form a segment 135 of the superconducting coupling loop 130.

Here however, and as above, one superconducting trace 172 (having a shorter trace length, corresponding to its respective JJ width 181) may directly couple to the second terminal 120, and an other superconducting trace 174 (having a longer trace length, including its respective JJ depth 183) may form a second segment 137 of the superconducting coupling loop 130. Preferably, SQUID 150 may be identical to SQUID 170, other than its electrical placement.

Advantageously, arranging the SQUIDs 150, 170 in this way may double an output voltage, while only increase the noise of the circuit by only √2, leading to a √2 increase in sensitivity. Further, this embodiment may require less wafer space than fabricating a second coupling loop with a second nanoSQUID on it and placing them in series with the first coupling loop.

Figure 7:
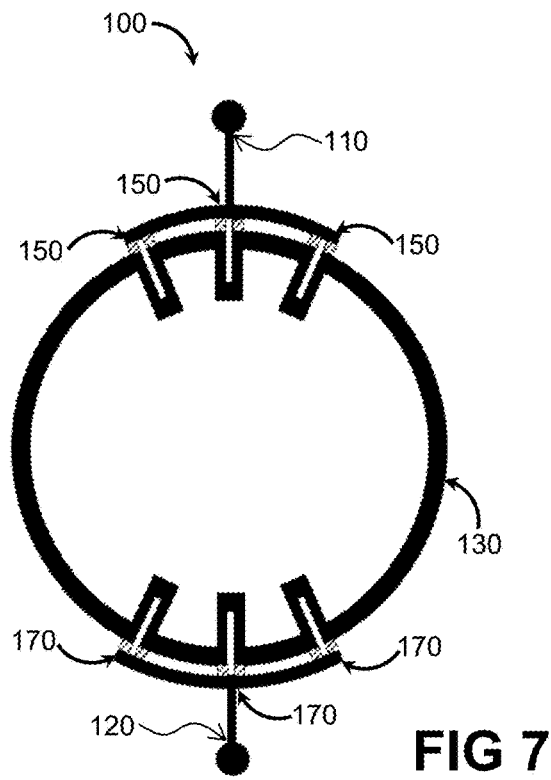
FIG. 7 shows parallel nanoSQUIDs at the input and output of a superconducting coupling loop, according to an exemplary embodiment of the present disclosure.
Figure 8:
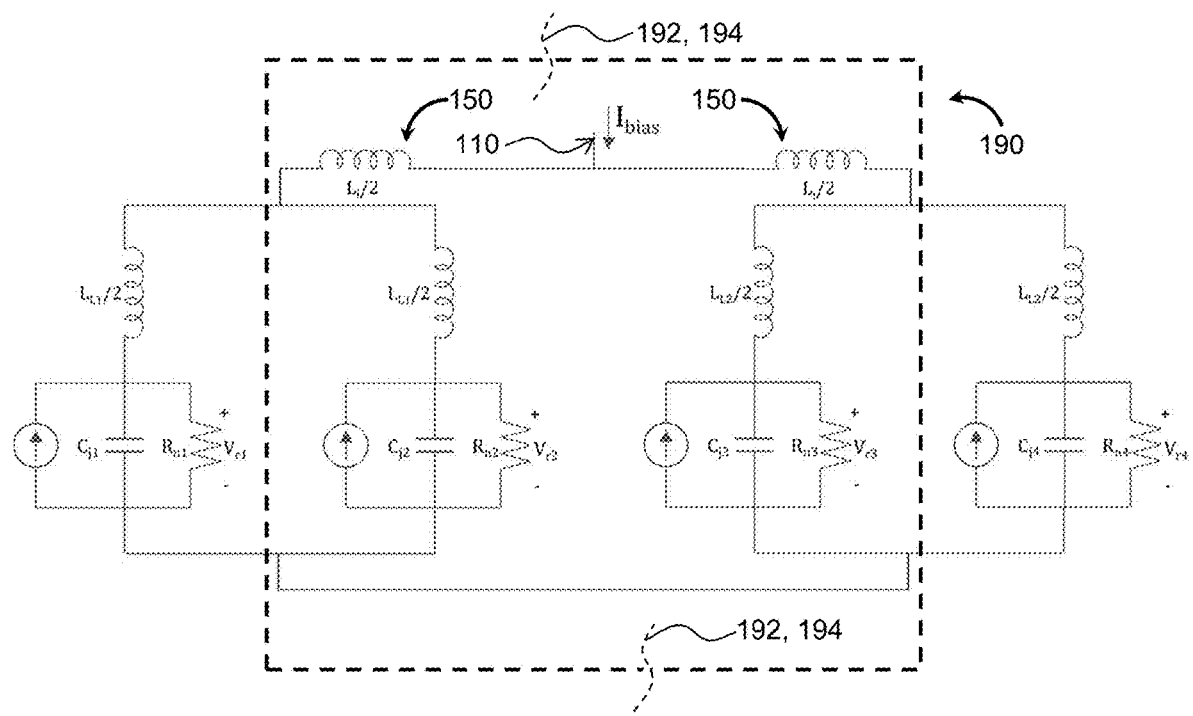
FIG. 8 schematically illustrates a RCSJ model for two DC SQUIDs in parallel, connected by an input line, according to an exemplary embodiment of the present disclosure.

FIG. 7 shows parallel nanoSQUIDs at the input and output (terminals 110, 120) of a superconducting coupling loop, according to an exemplary embodiment of the present disclosure. In particular, one or more additional nanoSQUIDs may be electrically coupled parallel with at least one of SQUIDs 150, 170 at the input and/or output of the superconducting coupling loop 130. Here, the parallel SQUIDs 150, 170 are also in series with each other. Contrast with FIG. 8, showing only two parallel SQUIDs 150.

As above, the electronic device 100 may include the first terminal 110, the second terminal 120, the superconducting coupling loop 130, and one or more SQUIDs 150, 170. Likewise, preferably, SQUID 150 may be identical to SQUID 170, other than its electrical placement.

According to one preferred embodiment, the electronic device 100 will include at least two SQUIDs 150 electrically coupled in parallel, and at least two SQUIDs 170 electrically coupled in parallel, with each parallel couple electrically coupled in series between the first terminal 110 and the superconducting coupling loop 130, and between the superconducting coupling loop 130 and the second terminal 120, respectively (analogously to FIG. 6).

According to one exemplary embodiment, and as shown, the electronic device 100 may include three SQUIDs 150 electrically coupled in parallel and at least two SQUIDs 170 electrically coupled in parallel, with each parallel couple electrically coupled in series between the first terminal 110 and the superconducting coupling loop 130, between the superconducting coupling loop 130 and the second terminal 120, respectively. Thus, the superconducting coupling loop 130 may have three parallel nanoSQUIDs coupled in series at both its input and the output ends. This circuit could be constructed with any number of nanoSQUIDs at the input or output ends, if they can physically fit into the area.

This arrangement may be advantageous because the noise of the nanoSQUIDs is reduced by $\sqrt{N}$, where N is the number of nanoSQUIDs in parallel. This reduction in noise may lead to a $\sqrt{N}$ increase in sensitivity. Further, this embodiment may require less wafer space than fabricating N additional superconducting coupling loops with nanoSQUIDs on them and placing them in parallel with the first superconducting coupling loop.

FIG. 8 schematically illustrates a RCSJ model for two DC SQUIDs in parallel, connected by an input line, according to an exemplary embodiment of the present disclosure. In particular, only two parallel SQUIDs 150 are shown. This is primarily for illustration purposes, buy may represent one alternate embodiment of the electronic device 100. As shown, the two parallel SQUIDs 150 are connected by an input line (e.g., to one of the first terminal 110 or the second terminal 120) with inductance Li. For clarity the label of the current sources in the Josephson Junctions has been removed.

An astute observer will note that the input connections to each of the parallel nanoSQUIDs may form a parasitic SQUID 190. In particular, the input line may create a third SQUID in the center which is considered the parasitic SQUID 190. This parasitic SQUID 190 is undesirable—the screening current that occurs in the parasitic SQUID 190 may diminish the screening current that flows through the Josephson Junction that is shared with the nanoSQUIDs. Therefore, any resultant parasitic SQUIDs 190 should be engineered to minimize their screening current. Generally, the parasitic SQUIDs 190 should be isolated, insolated, or otherwise disrupted electrically (e.g., via an electrical barrier 192), magnetically (e.g., via a magnetic flux shield 194), and/or physically (e.g., minimizing the coupling to the coupling loop while maximizing the total inductance of the parasitic SQUID 190). For example, the magnetic flux shield 194 may be embodied as a Lenz lens (FIG. 9) that is configured to keep flux from directly entering the parasitic SQUIDs 190.

According to one embodiment, a series of non-superconducting slits (electrical barrier 192) in the edge of perimeter of the coupling loop that are tangential to the edge of the coupling loop and between the coupling loop and the area enclosed by the parasitic SQUID 190 may be added. Advantageously, these slits may serve to reduce the amount of flux that is coupled into the parasitic SQUID 190.

Figure 9:
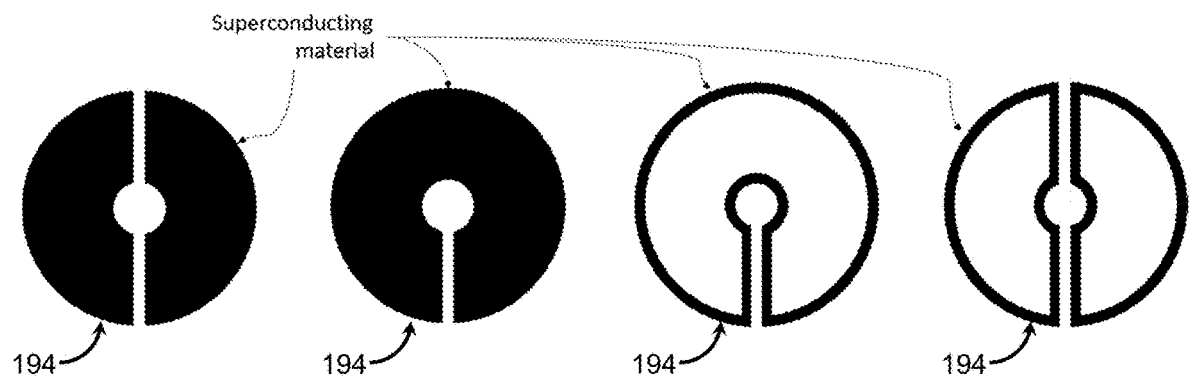
FIG. 9 illustrates four geometries for Lenz lenses made from superconducting material, according to an exemplary embodiment of the present disclosure.

FIG. 9 illustrates four geometries for Lenz lenses made from superconducting material, according to an exemplary embodiment of the present disclosure. As above, a magnetic flux shield 194 may be used to keep flux from directly entering the parasitic SQUID 190 (FIG. 8). As illustrated, according to one embodiment, a Lenz lens may be used as the magnetic flux shield 194. As shown, the exemplary geometries for Lenz lenses are made from a superconducting material. For reference, the dark area is superconducting while the white area is not. Each focuses flux into the white area in the center of the circles.

The Lenz lens (magnetic flux shield 194) may be configured to focus magnetic flux into the white region in the center of the circle, while blocking magnetic flux from entering any of the other regions that are covered or surrounded by superconductor. The Lenz lens can be fabricated on a second wafer and positioned next to the wafer containing nanoSQUID or SQUID electronics.

Figure 10:
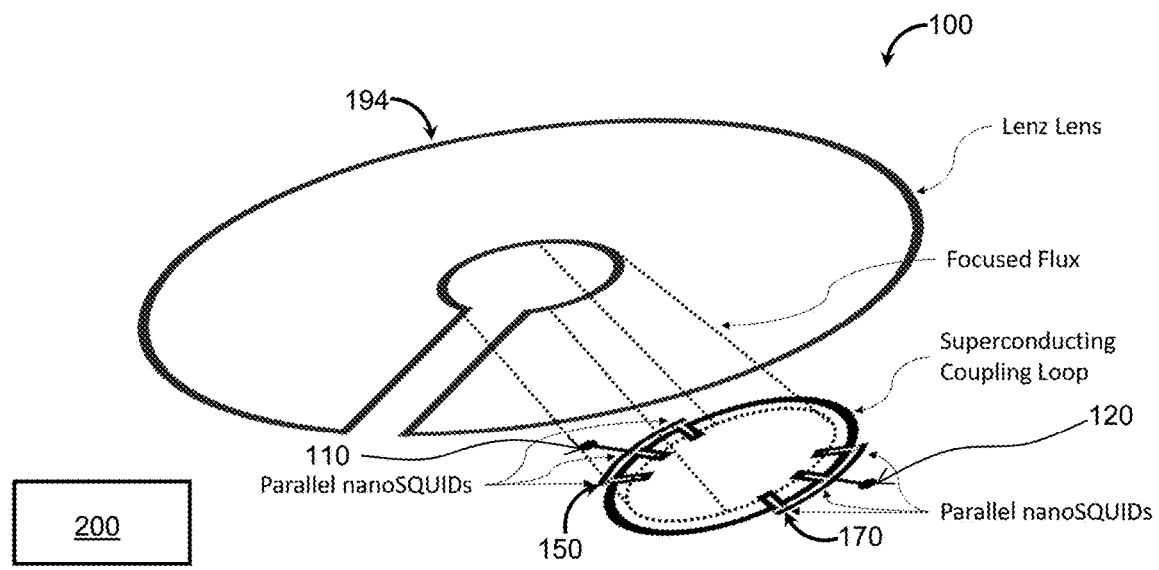
FIG. 10 illustrates a Lenz lens focusing magnetic flux into the coupling loop, according to an exemplary embodiment of the present disclosure.

According to this embodiment, the Lenz lens (magnetic flux shield 194) may be complementary to the features, because it can efficiently focus flux into the coupling loop, thereby increasing the effective area of the nanoSQUIDs. This is shown in FIG. 10. The Lenz lens shields flux from entering the secondary SQUIDs that are shown in FIG. 7. Further, a Lenz lens can shield flux from entering the Josephson Junctions on each nanoSQUID, which reduces the Fraunhofer effect in the nanoSQUID's flux to voltage transfer function. This Fraunhofer effect is undesirable because it can degrade the devices ability to operate in higher magnitude magnetic fields.

FIG. 10 illustrates a Lenz lens focusing magnetic flux into the coupling loop, according to an exemplary embodiment of the present disclosure. In particular, the Lenz lens (magnetic flux shield 194) may be configured to focus magnetic flux into the coupling loop. It may be further configured to shield flux from entering the parasitic SQUIDs 190 and the Josephson Junctions of the SQUIDs 150, 170.

The Lenz lens may also be configured to provide feedback or modulation to the SQUIDs 150, 170. Attaching electrodes to opposite sides of the inner circle will allow signals to be coupled into the SQUIDs 150, 170 via the Lenz lens (magnetic flux shield 194), which can be utilized to realize Flux Locked Loop (FLL) feedback. This solution will ensure that the FLL feedback signal is coupled into all the SQUIDs 150, 170 equally, and it will also save space on the wafer that contains the nanoSQUID electronics 200. The use of the Lenz lens as a flux focuser, flux shield, and as part of the FLL can be used with any arrangement of SQUIDs or nanoSQUIDs, with or without other flux focusing structures.

The nanoSQUID electronics 200 discussed in this disclosure can be used in a SQUID cascade, which exploits the SQUID's periodic voltage to flux transfer function to achieve extended dynamic range. The SQUID cascade is composed of multiple independent devices of different sensitivities, where each device can be composed of one or more of the nanoSQUID configurations previously described in this invention.

Alternatively, one or more, but not all, of the devices in the SQUID cascade might be fashioned from one or more of the nanoSQUID configurations described in the disclosure, while the other devices might be fashioned from other SQUID configurations or other magnetic field sensors. Each device in the SQUID cascade is responsible for encoding a defined number of bits of the signal. The least significant bits are encoded by the most sensitive device, the next least significant bits are encoded by a less sensitive device, and so on, until the full range of the signal can be encoded.

There may be some overlap in the dynamic range of two devices that are adjacent to each other in terms of sensitivity; for example, the most sensitive device might encode the least significant 16 bits of the signal, while the second most sensitive device might encode the tenth through the twenty-sixth least significant bits, providing six bits of overlap between the two devices. The least sensitive device might encode bits 20 through 36 of the signal, providing an overall dynamic range on the order of 216 dB. This could also be implemented with a number of devices that is greater or less than three devices. It could also be implemented in a configuration where each device is not responsible for encoding the same number of bits; for example, the most sensitive device might only be responsible for encoding eight bits, while the other devices are responsible for 14 bits. This can be done to relax the requirements on the electronics that require the most precision.

Figure 11:
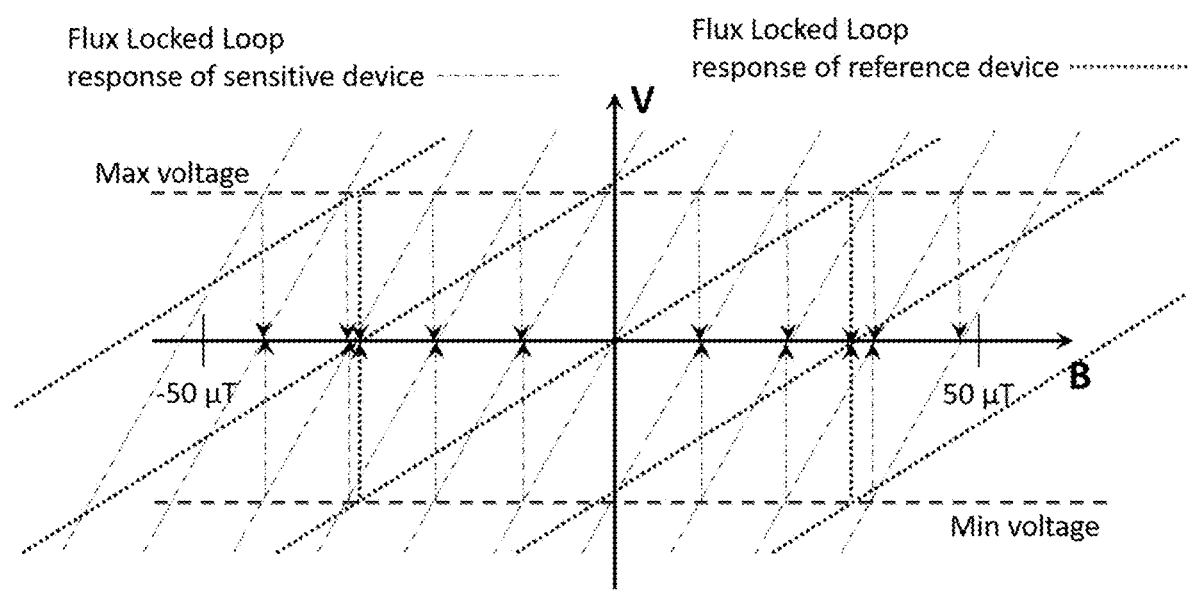
FIG. 11 illustrates a response of a Flux Locked Loop (FLL) output of a sensitive device and a reference device, according to an exemplary embodiment of the present disclosure.

FIG. 11 illustrates a response of a Flux Locked Loop (FLL) output of a sensitive device and a reference device, according to an exemplary embodiment of the present disclosure. When the FLL reaches the minimum or maximum voltage it resets to a new operating point. The less sensitive device is used to index into the more sensitive device. As will be understood by one having ordinary skill, the FFL may be incorporated in the nanoSQUID electronics 200 (FIG. 10) or elsewhere in a system incorporating the electronic device 100, and may vary substantially from application to application.

According to one embodiment, the electronic device 100 may be used as, integrated with, or otherwise applied as a Superconducting Quantum Interference Filter (SQIF). The SQIF combines many SQUIDs with different effective areas in series or parallel to create a sharp anti-peak at zero magnetic field in the SQIF's voltage vs. flux response. For example, the SQIF may incorporate any of the embodiments of the electronic device 100 discussed above and/or illustrated in the Figures.

According to one embodiment, the SQUIDs 150, 170 may be designed to have a minimum voltage response at zero magnetic field, and a periodic voltage response vs. flux as the magnetic field changes. The period of the voltage vs. flux response is a function of the effective area of the SQUID 150, 170. Accordingly, and in contrast to the discussion above, one or more SQUIDs 150, 170 may be unique or otherwise distinct from one or more others. For example, by giving a number of SQUIDs 150, 170 different effective areas, and by combining their responses, the voltage vs. flux response will have a sharp anti-peak at zero magnetic field.

Control electronics (e.g., nanoSQUID electronics 200) can be used to bias the SQIF at the steepest region of the anti-peak, where any received magnetic flux will induce a linear response in the SQIF output. SQIFs can also be used to create periodic voltage vs. flux responses by selecting the correct combination of SQUIDs 150, 170 with the correct effective areas.

According to one embodiment, the electronic device 100 may be used or integrated with control electronics, or otherwise applied to allow the SQIF voltage vs. flux response to be achieved. In particular, the electronic device 100 may increase or decrease the length of the SQUIDs 150, 170 so that their kinetic and geometric inductance increase or decrease. This in turn will increase or decrease the effective area of the SQUIDs 150, 170. According to one embodiment, the SQIF can also be created as a system by placing an array of superconducting coupling loops 130 in parallel, series, or a combination of the two, where each superconducting coupling loop 130 contains SQUIDs 150, 170 in parallel, series, or a combination of the two, as described above. For example and as discussed above, a series SQIF system may be represented by arraying a plurality of the electronic devices 100 (shown in the figures) in series (i.e., electrically coupling the second terminal 120 of a first electronic device 100 to the first terminal 110 of a subsequent electronic device 100, and so on). Also for example, and as discussed above, a parallel SQIF system may be represented by arraying a plurality of the electronic devices 100 (shown in the figures) in parallel (i.e., electrically coupling the first terminal 110 of each electronic device 100 together, and electrically coupling the second terminal 120 of each electronic device 100 together).

As shown, in these embodiments, the electronic device 100 may benefit from the fact that the SQUIDs 150, 170 or SQUID array's voltage response does not saturate. The FLL that keeps the SQUID at a linear operating point will saturate, but it can be dis-engaged, allowing the SQUIDs 150, 170 to run, and then re-engaged in time to take a new sample. As shown, when the output of the FLL reaches a maximum or minimum voltage, it disengages and then re-engages, resetting the operating point. Then the FLL will linearize the device's output again and run until the FLL output saturates at the minimum or maximum voltage.

While the voltage output of only two devices is shown, it is understood that more devices may be used to achieve even higher dynamic range. Because there is ambiguity associated with the absolute magnetic field that a sensitive device is reading, the less sensitive device is used to index into the periodic response of the more sensitive device. This removes the ambiguity. The least sensitive device should be able to make a coarse measurement of the full range of the signal that the device will see. This coarse measurement indexes into the next device in the cascade, which indexes into the next device, and so on, providing an extended dynamic range.

The Inventor has further discovered an improved SQUID flux focusing structure. In particular, a magnetic flux pickup can be coupled to a SQUID or nanoSQUID that incorporates an input coil made of a superconducting tape, which may be embodied in an electronic device for sensing magnetic fields.

Generally, some of the most sensitive magnetic field measurement systems use one or more Superconducting Quantum Interference Devices (SQUIDs) to take the magnetic field measurement. A SQUID can be formed when a superconducting loop has one or more weak links called Josephson Junctions (JJs). Magnetic flux that passes through the loop results in current flowing around the loop, which causes a measurable voltage across the JJ. However, some-times the SQUID's length and width can be smaller than 100 microns, which limits the amount of flux that enters the SQUID.

Also, a SQUID can be coupled to a larger magnetic flux pickup loop to increase the amount of magnetic flux measured. In particular, the pickup loop is connected in series with an input coil. When magnetic flux enters the pickup loop, it causes a current to flow through the input coil, which is preferably smaller than the pickup loop and has more than one turn. When the current flows through the input coil, it generates a second magnetic flux. The input coil can be placed over the SQUID to cause the second magnetic flux to enter the SQUID. Alternately, and as discussed above, the input coil can be placed over a superconducting coupling loop of a SQUID to cause the second magnetic flux to enter the SQUID via the superconducting coupling loop.

Increasing the amount of magnetic flux that enters a SQUID by using flux focusing structures can be thought of as increasing the size of the SQUID; the area of a SQUID that would capture the increased amount of flux is called the effective area. The effective area is larger than the SQUID's geometric area when flux focusing structures are used. The larger the SQUID's effective area, the more magnetic flux will pass through the SQUID.

To illustrate, the effective area of a SQUID with a pickup loop is given in Equation (1).

$$A_{\mathit{eff},spl} \cong \frac{k\sqrt{L_{SQUID}L_{inputcoil}}}{L_{inputcoil} + L_{pickuploop}} A_{pickuploop} \quad \text{Equation (1)}$$

Where:
A_eff,spl is the effective area of a SQUID with a pickup loop,
k is the coupling constant between the SQUID and the input coil,
A_pickup loop is the geometric area of the pickup loop,
L_SQUID is the inductance of the SQUID,
L_input coil is the inductance of the input coil, and
L_pickup loop is the inductance of the coupling loop.

To maximize the amount of magnetic flux that enters the SQUID from the input coil, the coupling constant k should be maximized. This is done by making the input coil the same size as the SQUID. Alternatively, the SQUID can be fabricated in a larger superconducting structure, the same size as the input coil, which focuses flux from input coil into the SQUID. This has the disadvantage that it often increases the inductance of the SQUID, which increases the SQUID's noise floor. The effect of inductance on SQUID noise is shown in Equation (2) below.

Analysis of Equation (1) shows that matching the inductance of the input coil with the pickup loop will optimize the effective area of the SQUID for a given pickup loop area and inductance. By using more than one turn in the input coil, the total inductance of the input coil can be matched with the pickup loop, even though the input coil is geometrically smaller than the pickup loop.

In addition, using a pickup loop and input coil allows the magnetic field measurement to be taken in at the location of the pickup coil, rather than the location of the SQUID. This may be advantageous for certain system designs.

Figure 12:
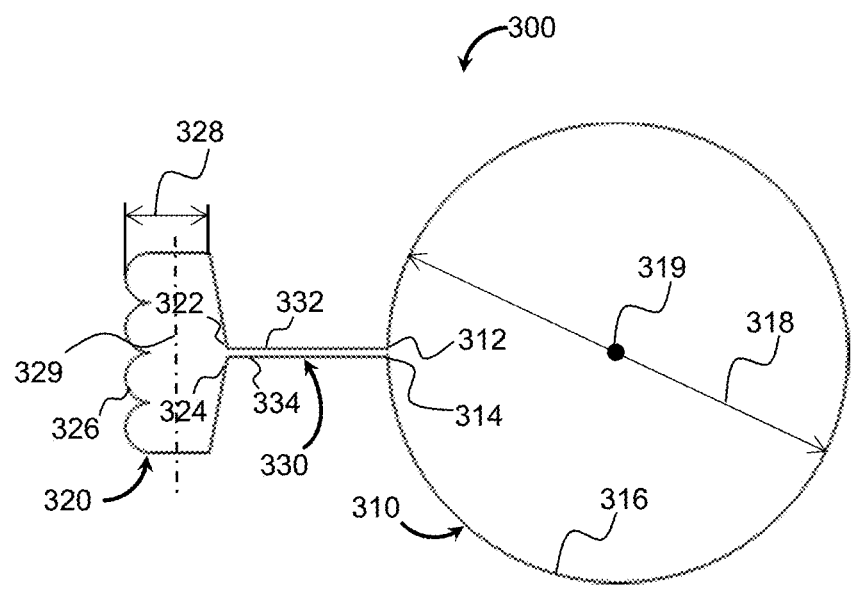
FIG. 12 is a schematic diagram of a magnetic flux pickup, according to an exemplary embodiment of the present disclosure.

FIG. 12 is a schematic diagram of a magnetic flux pickup, according to an exemplary embodiment of the present disclosure. As shown, a magnetic flux pickup 300 may include a magnetic flux pickup loop 310 and an input coil 320. For reference, as shown schematically, the magnetic flux pickup loop 310 has a pickup loop center axis 319 (illustrated as exiting the plane), and the input coil 320 has an input coil center axis 329.

Generally, the magnetic flux pickup loop 310 is a superconducting loop configured to be placed in a magnetic field and pickup magnetic flux. Structurally, the magnetic flux pickup loop 310 may generally include a first pickup end 312, a second pickup end 314, and an open loop 316, with the open loop 316 extending between the first pickup end 312 and the second pickup end 314 about the pickup loop center axis 319. The open loop 316 may substantially surround the pickup loop center axis 319, for example, circumscribing at least 350 degrees about the pickup loop center axis 319.

The magnetic flux pickup loop 310 is made of a superconducting material. In embodiments the superconducting material may be a high temperature superconducting material. For convenience, the open loop 316 may be characterized by a pickup loop diameter 318 defined as an average diametrical distance between opposing sides of the open loop 316. According to one embodiment, the pickup loop diameter 318 of the magnetic flux pickup loop 310 may preferably be between 50 millimeters and 150 millimeters. It should be understood that, while the open loop 316 is conveniently drawn as round, other shapes and geometries are contemplated. As such, equivalent dimensions may be preferred, rather than identical dimensions.

Generally, the input coil 320 is a superconducting coil electrically coupled to the magnetic flux pickup loop 310, and configured to concentrate and transfer magnetic flux picked up from the magnetic flux pickup loop 310 to a SQUID. Structurally, the input coil 320 may generally include a first coil terminal end 322 and a second coil terminal end 324, and a coil 326 of at least one loop, with the coil 326 extending between the first coil terminal end 322 and the second coil terminal end 324 about the input coil center axis 329. The coil 326 may substantially surround the input coil center axis 329, for example, circumscribing at least 350 degrees about the input coil center axis 329. Further, the coil 326 may include a plurality of loops about the input coil center axis 329 (e.g., greater than 710 degrees). Preferably, the coil 326 may include two to twenty loops. According to one embodiment, the plurality of loops may have a substantially similar diameter or distance from the input coil center axis 329, and thus be "vertically" stacked, one loop above another. According to a preferred embodiment, the plurality of loops may be radially stacked as concentric rings about the input coil center axis 329.

The input coil 320 is made of a superconducting material. In embodiments the superconducting material may be a high temperature superconducting material, and may be the same material as the magnetic flux pickup loop 310. Preferably, the input coil 320 is at least partially made of a superconducting tape. For reference, the superconducting tape is understood as having a tape width and tape thickness, as commonly understood for tapes. For example, where the plurality of loops of the coil 326 are radially stacked as concentric rings spiraling radially about and relative to the input coil center axis 329, the tape may be "tightly rolled" about a first loop or inner ring having a minimum diameter. To further illustrate, each loop may have an average diameter that is approximately twice the tape thickness less than a radially adjacent inner loop and/or approximately twice the tape thickness less than a radially adjacent outer loop. This is particularly advantageous as the tape may be wound into a tighter loop and a greater number of loops may be located in a given volume.

For convenience, the input coil 320 may be characterized by a coil diameter 328 defined as an average diametrical distance between opposing sides of the coil 326. As illustrated, the first terminal coil end 322 is electrically coupled to the first pickup end 312 of the magnetic flux pickup loop 310. Similarly, the second coil terminal end 324 is electrically coupled to the second pickup end 314 of the magnetic flux pickup loop 310.

According to one embodiment, the magnetic flux pickup 300 may be configured such that the magnetic flux pickup loop 310 can be remotely located from the input coil 320, and thus the SQUID (not shown). In particular, the magnetic flux pickup 300 may further include a pair of extension arms 330 configured to electrically couple the magnetic flux pickup loop 310 to the input coil 320, while each is remotely located from the other.

Structurally, and as shown, the pair of extension arms 330 may be two independent members 332, 334 made of a superconducting material, with each extending between and electrically coupling the first terminal coil end 322 of the input coil 320 to the first pickup end 312 of the magnetic flux pickup loop 310, and the second terminal coil end 324 of the input coil 320 to the second pickup end 314 of the magnetic flux pickup loop 310, respectively. In embodiments the superconducting material may be a high temperature superconducting material, and may be the same material as the magnetic flux pickup loop 310 and/or the input coil 320. For example, according to one embodiment, the pair of extension arms 330 may be at least partially made of a superconducting tape.

Beneficially, the pair of extension arms 330 may provide for SQUIDs (e.g., high temperature SQUIDs to use a remotely located pickup loop. For example, each of the pair of extension arms 330 may be at least 10 times longer than the coil diameter 328 of the input coil 320.

Figure 13:
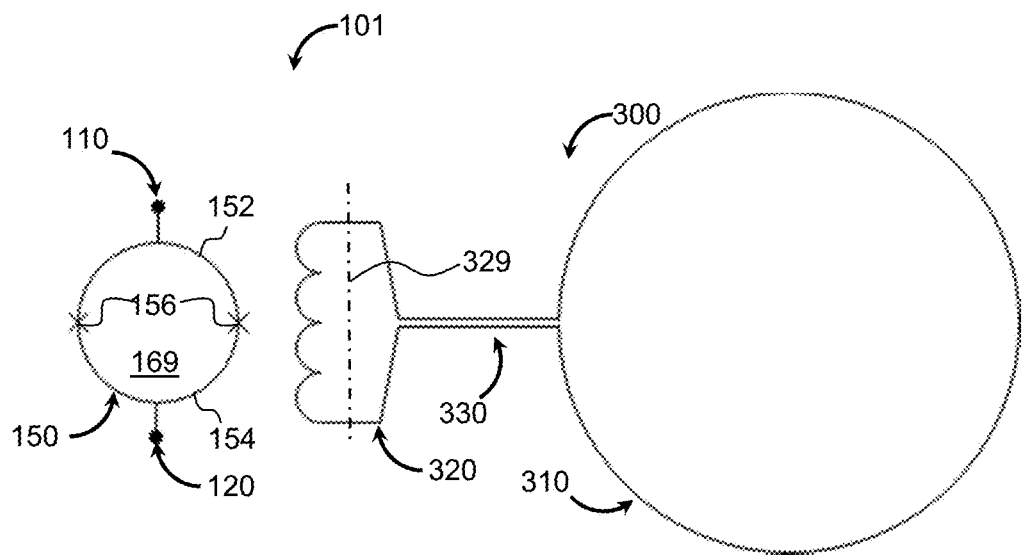
FIG. 13 is a schematic diagram of the magnetic flux pickup for FIG. 12 coupled to a SQUID, according to an embodiment of the present disclosure.

FIG. 13 is a schematic diagram of the magnetic flux pickup for FIG. 12 coupled to a SQUID, according to an embodiment of the present disclosure. Here, an electronic device 101 for sensing magnetic fields is shown, which may include one or more features of the electronic device 100 discussed above. As shown, the electronic device may include the magnetic flux pickup 300 and a Superconducting Quantum Interference Device (SQUID) 150, where the magnetic flux pickup 300 is configured to concentrate and transfer magnetic flux picked up from the magnetic flux pickup loop 310 to the SQUID 150. In particular, the electronic device 101 may include a first electronic device terminal 110, a second electronic device terminal 120, the SQUID 150, and the magnetic flux pickup 300.

As discussed above, the SQUID 150 may include the first superconducting trace 152 extending between two its first opposing ends, the second superconducting trace 154 extending between its two second opposing ends, and the pair of Josephson Junctions 156 electrically coupled in parallel between each of the first superconducting trace 152 and the second superconducting trace 154 at the first opposing ends and second opposing ends of the first superconducting trace 152 and the second superconducting trace 154, respectively. Also as above, the first superconducting trace 152 and the second superconducting trace 154 together may form the aperture 169. The SQUID 150 is electrically coupled in series between the first terminal 110 via the first superconducting trace 152, and the second terminal 120 via the second superconducting trace 154.

Also as above the magnetic flux pickup 300 may be made of a superconducting material, and include the magnetic flux pickup loop 310 and the input coil 320. The magnetic flux pickup loop 310 and the input coil 320 may be made of the same superconducting material or different superconducting materials. The input coil 320 has the input coil center axis 329 and at least one loop about both the input coil center axis 329.

Further, the input coil 320 may be aligned with an edge of the SQUID 150, such that the input coil 320 is positioned proximate the SQUID 150, and the input coil center axis 329 of the input coil 320 passes through the aperture 169 of the SQUID 150. Preferably, each loop of the input coil 320 will be shaped, sized, and dimensioned substantially similar to the first superconducting trace 152 and the second superconducting trace 154, such that they substantially overlap when projected to a common plane normal to the input coil center axis 329. It should be understood, the input coil 320 is shown schematically to the side of the SQUID 150 for convenience only, but would aligned similar to FIG. 18.

Also, the SQUID's inductance may be reduced to decrease its noise. This is shown in Equation (2).

$$S_\varphi \cong 16 \sqrt{\frac{k_B T}{R}} L_{SQUID} \qquad \text{Equation (2)}$$

Where:
S_φ is the Power Spectral Density (PSD) of the noise of a SQUID,
k_B is Boltzmann's constant,
T is the temperature of the device,
R is the normal resistance of the JJs, and
L_SQUID is the inductance of the SQUID.

Equation (2) shows that magnitude of the noise PSD is proportional to the inductance. In order to decrease the inductance, the geometric area of the SQUID must be decreased. The smallest SQUIDs that can be created using nanofabrication techniques are nanoSQUIDs, where at least one of the dimensions of the SQUID is under 1000 nanometers.

Figure 14:
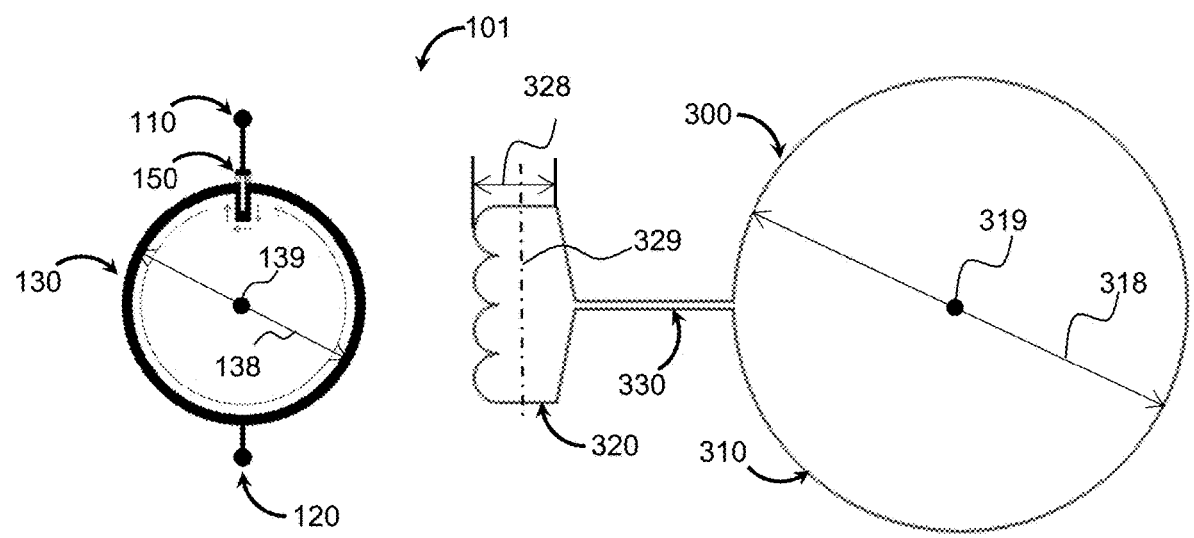
FIG. 14 is a schematic diagram of the magnetic flux pickup for FIG. 12 coupled to a SQUID utilizing a coupling loop, according to another embodiment of the present disclosure.

FIG. 14 is a schematic diagram of the magnetic flux pickup for FIG. 12 coupled to an exemplary SQUID and utilizing a coupling loop, according to another embodiment of the present disclosure. As above, the electronic device 101 may include the first electronic device terminal 110, the second electronic device terminal 120, the SQUID 150, and the magnetic flux pickup 300, where the magnetic flux pickup 300 may include the magnetic flux pickup loop 310 and the input coil 320, as well as the pair of extension arms 330.

As shown, the electronic device 101 may further include the SQUID coupling loop 130 as discussed above. In particular, the SQUID coupling loop 130 is also made of a superconducting material, is conveniently characterized here by a coupling loop diameter 138, has a coupling center axis 139, and shares part of a circuit with the SQUID 150. In particular and as discussed above, to increase the effective area for High Temperature Superconductor (HTS) SQUIDs, the HTS SQUID (e.g., SQUID 150) may be electrically coupled to and share an edge or section of a larger coupling loop (e.g., SQUID coupling loop 130). Also as discussed above, the SQUID coupling loop 130 may be integrated with the second superconducting trace such that the second superconducting trace forms a first segment of the superconducting loop, with the SQUID coupling loop 130 electrically coupled in series between the first terminal 110 via the second superconducting trace and the second terminal 110. It should be noted, while the electronic device 101 is illustrated with the basic SQUID 150 and SQUID coupling loop 130 of FIG. 5, all other variations are contemplated.

As shown, the SQUID coupling loop 130 may be shaped into a closed loop about the coupling center axis 139. The SQUID coupling loop diameter 138 may be conveniently defined as an average diametrical distance between opposing sides of the closed loop. While the SQUID coupling loop 130 is conveniently illustrated as a circle, many other shapes and forms are contemplated, particularly when integrated directly with a circuit board. Also, using the coupling loop diameter 138, the pickup loop diameter 318, and the coil diameter 328, as reference dimensions, the geometric areas of the SQUID coupling loop 130, the magnetic flux pickup loop 310 and the input coil 320 may be determined.

Generally, the magnetic flux pickup 300 may be configured to concentrate and transfer magnetic flux picked up from the magnetic flux pickup loop 310 to the SQUID coupling loop 130, rather than directly to the SQUID 150. In particular, the SQUID coupling loop 130 is configured to couple flux into the SQUID primarily through kinetic inductance rather than geometric inductance. The use of the coupling loop may provide greater performance by providing the SQUID with a greater effective area. This is shown in Equation (3) below.

$$A_{\mathit{eff},scl} \cong A_s + A_{couplingloop} \frac{L_{SQUID}}{L_{couplingloop}} \quad \text{Equation (3)}$$

Where:
A_eff,scl is the effective area of the SQUID with a coupling loop,
A_s is the geometric area of the SQUID,
A_coupling loop is the geometric area of the coupling loop,
L_SQUID is the inductance of the SQUID, and
L_coupling loop is the inductance of the coupling loop.

This structure may be particularly beneficial where the SQUID is embodied as a nanoSQUID, also as discussed above. Equation (3) is still valid for the situation where the SQUID is a nanoSQUID. To illustrate, the smaller the SQUID is, the less magnetic flux will pass through its loop. To increase the effective area of a nanoSQUID, the nanoSQUID can be fabricated on the edge of a coupling loop. Further, it can be done in HTS, since it requires only a single layer. According to one embodiment, the SQUID 150 may be fabricated along the edge of the coupling loop. In particular, the SQUID coupling loop 130 may be fabricated on the same single layer integrated circuit as the SQUID 150, sharing a common portion of the superconducting trace. This couples flux from the SQUID coupling loop 130 into the SQUID 150, thereby increasing its effective area.

Here, the inductance of the SQUID 150 is smaller than the inductance of the SQUID coupling loop 130, and thus the coupling is not optimal. In particular, the mismatch in between the nanoSQUID's inductance and the loop's inductance results in a proportionally less efficient transfer of flux from the coupling loop to the nanoSQUID. Put another way, the larger the coupling loop, the more flux it will capture, but the less efficiently it will transfer that flux to the nanoSQUID. Accordingly, additional modifications may be made. Generally, the closer the inductance of the SQUID 150 and SQUID coupling loop 130 are, the more effectively flux from the SQUID coupling loop 130 will enter the SQUID 150. Notwithstanding, the SQUID coupling loop 130 must still be large to increase the amount of flux that enters it, but the larger SQUID coupling loop 130 is, the larger its inductance will become.

Figure 15:
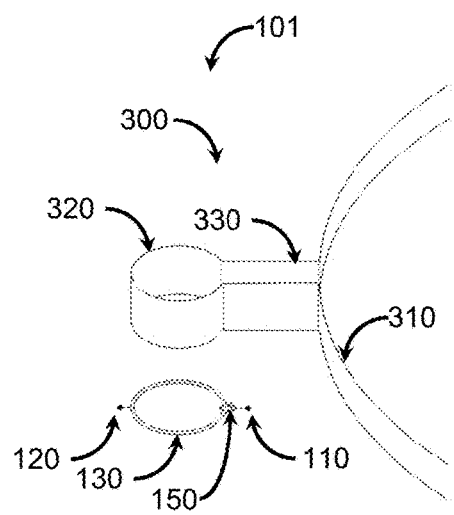
FIG. 15 is a detail diagram of a magnetic flux pickup incorporating tape, coupled to a nanoSQUID, according to one embodiment of the present disclosure.

FIG. 15 is a detail diagram of a magnetic flux pickup incorporating tape, coupled to a nanoSQUID, according to one embodiment of the present disclosure. As above, the electronic device 101 may include the first electronic device terminal 110, the second electronic device terminal 120, the SQUID 150, the SQUID coupling loop 130, and the magnetic flux pickup 300, where the magnetic flux pickup 300 may include the magnetic flux pickup loop 310, the input coil 320, and the pair of extension arms 330.

According to one embodiment, the SQUID 150 may be a nanoSQUID as discussed above. In particular, referring to FIG. 3, the first superconducting trace 152 of the SQUID 150 may have at least a first trace length 162 (as measured between one junction end of each of the first pair of Josephson Junctions 156) being less than 999 nm. According to one embodiment, and as illustrated, the second superconducting trace 154 may have the second trace length 164 (as measured between an other junction end of each of the first pair of Josephson Junctions 156) being at least twice the first trace length.

Returning to FIG. 15, while there are potential benefits to using both a nanoSQUID and a pickup loop, there are a variety of challenges. In particular, merely decreasing the size of the SQUID (i.e., using a nanoSQUID) and increasing the size of the pickup loop may invoke performance depreciating interactions. As result, the inventor has discovered that additional modifications may be made to mitigate or overcome these and other challenges.

Generally, here, the area of a loop may be expressed as being proportional to the square of its inductance, expressed below in Equation (4).

$$A_L \cong \frac{C_L L_L^2}{n^2} \quad \text{Equation (4)}$$

Where:
A_L is the area of the loop,
C_L is a constant of proportionality,
n is the number of turns in the loop, and
L_L is the loop's inductance.

Substituting Equation (4) into Equation (1) above, and using n=1 gives Equation (5):

$$A_{\mathit{eff},spl} \cong \frac{k\sqrt{L_{SQUID}L_{inputcoil}}}{L_{inputcoil} + L_{pickuploop}} C_{pickuploop} L_{pickuploop}^2 \quad \text{Equation (5)}$$

Where: A_eff,spl remains the effective area of a SQUID with a pickup loop.

Similarly, Equation (6) is the application of Equation (5) to a coupling loop.

$$A_{\mathit{eff},cl} \cong \frac{k\sqrt{L_{couplingloop}L_{inputcoil}}}{L_{inputcoil} + L_{pickuploop}} C_{pickuploop} L_{pickuploop}^2 \quad \text{Equation (6)}$$

Where: A_eff,cl is the effective area of the coupling loop.

Next, combining Equations (6) and (3) yields the effective area of a SQUID on the edge of the coupling loop. This is shown in Equation (7) below.

$$A_{eff,scl,pl} \cong A_s + \frac{k\sqrt{L_{couplingloop}L_{inputcoil}}}{L_{inputcoil} + L_{pickuploop}} C_{pickuploop} L_{pickuploop}^2 \frac{L_{SQUID}}{L_{couplingloop}}$$ Equation (7)

Where: A_eff,scl,pl is the effective area of a SQUID fabricated on the edge of a coupling loop with a pickup loop and input coil over the coupling loop.

Next, Equation (7) can be rearranged into simplified Equation (8).

$$A_{eff,scl,pl} \cong A_s + \frac{k\sqrt{L_{inputcoil}}}{L_{inputcoil} + L_{pickuploop}} C_{pickuploop} L_{pickuploop}^2 \frac{L_{SQUID}}{\sqrt{L_{couplingloop}}}$$ Equation (8)

Accordingly, Equation (8) shows that reducing the inductance of the SQUID coupling loop 130 (L_coupling loop) can increase the effective area of the SQUID (A_eff,scl,pl). This can be accomplished by decreasing its size. However, as the size of the SQUID coupling loop 130 decreases (particularly on orders associated with a nanoSQUIDs), manufacturability of an appropriate input coil becomes an issue.

Further, when a SQUID is made from a Low Temperature Superconductors (LTS) such as Niobium, which is a metal, the SQUID 150 and the input coil 320 can be fabricated on a multi-layer integrated circuit using microfabrication techniques. The magnetic flux pickup loop 310 can also be made from LTS metal wire and connected to the input coil 320 on the integrated circuit. However, if the SQUID 150 is fashioned from High Temperature Superconductors (HTS), which is a ceramic, it is more difficult to create a multi-layer integrated circuit. This is because when an additional layer of superconductor is deposited, it is not easy to make high quality connections between layers.

Also, as noted earlier, multi-turn input coils are very difficult to fabricate on the same chip as an HTS SQUID. However, it is possible to make a pickup loop and multi-turn input coil out of HTS by using an HTS tape. The challenge is that the tapes used by industry cannot be coiled in a tight diameter. When they are coiled very tightly, the superconductor experiences stress and its performance degrades. Thus, a minimum diameter of several centimeters is common. This makes matching the input coil with the SQUID impractical.

Recently a novel, ultra-thin film HTS tape with a bend diameter D of under 1 millimeter has been demonstrated. It has been fabricated by removing a portion of the tape's substrate, so that the HTS portion is in the neutral axis of the tape. By reducing the substrate thickness, and carefully engineering the thickness of the different layers of the tape so that each component's Young's modulus is matched, the tape can be made to be flexible without degradation of its performance. Furthermore, reducing the substrate thickness results in a thinner tape, which may have a thickness of 15-30 μm.

According to one embodiment, the input coil 320 may be fashioned from an ultra-thin HTS tape (e.g., as recently described in U.S Pat. App. Pub. No. 2018/0151792 by Selvamanickam). In particular, the ultra-thin HTS tape may have a tape width and tape thickness, with the tape width being at least 1 millimeter, and the tape thickness being less than 0.050 millimeter. Further, the coil diameter of the input coil 320 may be less than 1 millimeter.

Here, the input coil 320 is arranged as a single loop (n=1, circumscribing at least 350 degrees about the pickup loop center axis), however, as discussed below, multiple tightly wound loops are contemplated (ref., FIG. 17). Thus, the ultra-thin film HTS tape with very small bend diameter (D<1 mm) may be used to fashion an improved multi-turn input coil (and pickup loop). Alternately, additional portions or the entire magnetic flux pickup 300 may be made of the ultra-thin film HTS tape. For example, the input coil 320 may be made from an ultra-thin HTS tape, that consists of one or more turns, and that is in series with the magnetic flux pickup loop 310 made from an ultra-thin HTS tape (as well as the pair of extension arms 330 made from an ultra-thin HTS tape).

As described above, the input coil 320 can be placed over SQUID coupling loop 130 that has the SQUID 150 (SQUID, or nanoSQUID), fabricated on its edge. Beneficially, this arrangement may result in a higher Signal to Noise Ratio (SNR) than using an HTS SQUID with a coupling loop, or even using an HTS SQUID with a coupling loop, a pickup loop, and an input coil made from conventional, thick HTS tape that has a bend diameter larger than D of the ultra-thin film HTS tape.

According to one embodiment, to maximize the coupling constant k, the input coil 320 and the SQUID coupling loop 130 may shaped, sized, and dimensioned to substantially match each other. In particular, the input coil 320 and the SQUID coupling loop 130 may have the same shape (here round), and the coil diameter 328 (FIG. 14) and the coupling loop diameter 138 (FIG. 14) may be within 25% of each other. Preferably, the input coil 320 may be substantially the same size and shape as the SQUID coupling loop 130 (e.g., within 10%). According to one embodiment, the SQUID coupling loop 130 may be made from an HTS circuit on a chip that is geometrically matched to the input coil the input coil 320. Advantageously, using a nanoSQUID instead of a regular SQUID on the edge of the coupling loop in conjunction with ultra-thin, highly flexible HTS tape pickup loop and input coil may provide a higher effective area as well as lower noise floor.

Figure 16:
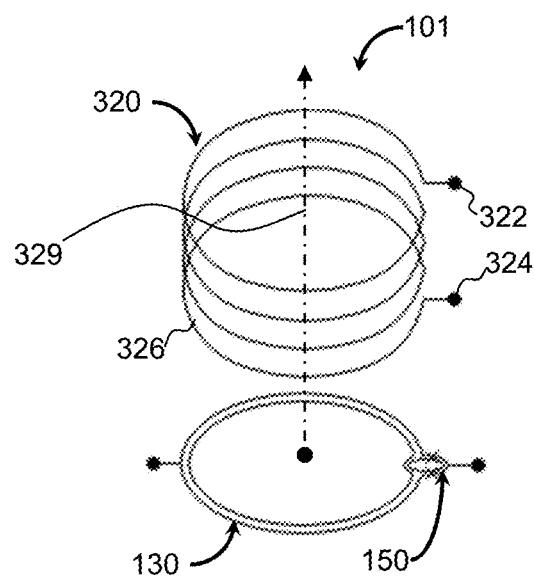
FIG. 16 is a schematic diagram of a multi-loop input coil coupled to a SQUID, according to one embodiment of the present disclosure.

FIG. 16 is a schematic diagram of a multi-loop input coil coupled to a SQUID, according to another embodiment of the present disclosure. As above, the input coil 320 may include the coil 326 extending between the first coil terminal end 322 and the second coil terminal end 324 about the input coil center axis 329, and in alignment with the SQUID coupling loop 130 (i.e., coaxial). As shown, the coil 326 of the input coil 320 may include a plurality of loops. In particular, the coil 326 may include two to twenty loops. According to one embodiment (shown), the plurality of loops may have a substantially similar diameter or distance from the input coil center axis 329, and thus be "vertically" stacked, one loop above another.

Figure 17:
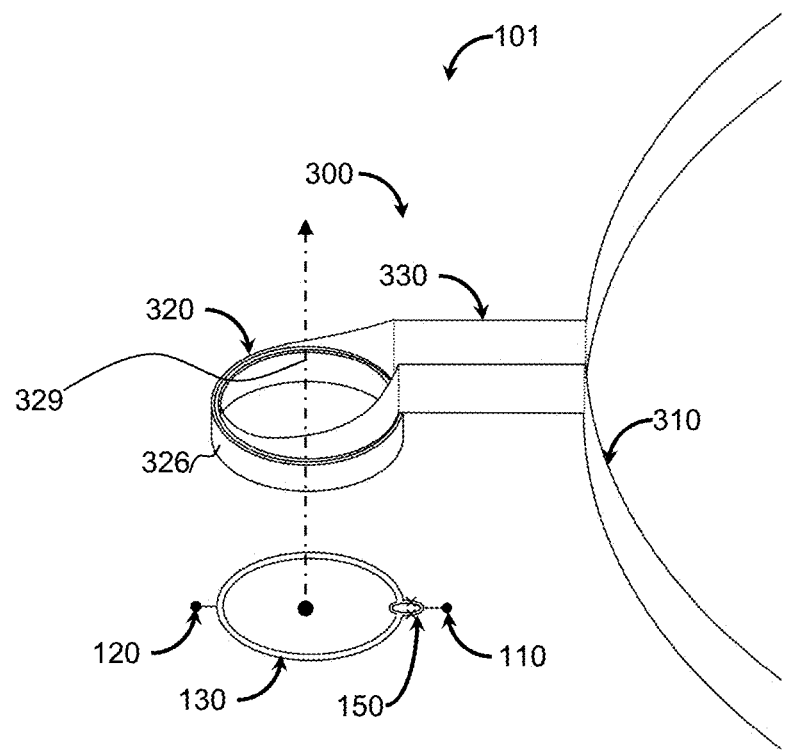
FIG. 17 is a detail diagram of a multi-loop tape input coil of a magnetic flux pickup coupled to a SQUID, according to one embodiment of the present disclosure.

FIG. 17 is a detail diagram of a multi-loop tape magnetic flux pickup coupled to a SQUID, according to one embodiment of the present disclosure. As above, the electronic device 101 may include the first electronic device terminal 110, the second electronic device terminal 120, the SQUID 150, the SQUID coupling loop 130, and the magnetic flux pickup 300, where the magnetic flux pickup 300 may include the magnetic flux pickup loop 310, the input coil 320, and the pair of extension arms 330.

As shown, the plurality of loops may be tightly wound about the input coil center axis 329, and thus be "radially" stacked, one loop around another, as concentric rings about the input coil center axis 329 and spiraling outward, were the tape width is oriented parallel with the input coil center axis 329. Further, the magnetic flux pickup 300 and the SQUID coupling loop 130 may be fixed in a position proximate and one directly over the other. While both are shown having a generally circular shape (plan view), other matching shapes are contemplated, including, but not limited to, curved, linear, and any combination thereof.

This embodiment can be very beneficial for matching the inductance of the input coil 320 with the inductance of magnetic flux pickup loop 310, while maintaining a high coupling constant between the magnetic flux pickup loop 310 and the input coil 320. In particular, by making the magnetic flux pickup loop 310 out of ultra-thin, highly flexible HTS tape, and then winding it tightly about the input coil center axis 329 may provide for the input coil diameter to be decreased relative to a regular HTS tape. Doing this is advantageous because it allows the coupling loop inductance to be decreased while maintaining a high coupling constant between the coupling loop and input coil.

As shown, the electronic device 101 includes the input coil 320 is arranged as a multiple loop (n>1) coil, having tightly wound loops of ultra-thin film HTS tape with very small bend diameter (D<1 mm). Additionally, the magnetic flux pickup loop 310 and the pair of extension arms 330 may also be made from the ultra-thin HTS tape. Each component may be made of the same superconducting material, different superconducting material, or any combination thereof.

As above, the coil 326 of the input coil 320 may preferably include from two to twenty loops. However, in other embodiments, a radial stacked coil with as many loops may be unworkable in aligning and matching the input coil 320 to the SQUID coupling loop 130, particularly where nanoSQUIDs are employed. Here however, since the tape is ultra-thin, it allows the input coil 320 to include more loops for a specified coil outer diameter.

To illustrate, for a given minimum bend diameter (ID) of 0.51 mm and a tape thickness 0.015 mm, two to twenty loops may result in an outer diameter (OD) of approximately 1.06 mm to 1.6 mm with a combined (all loops) coil thickness of 0.03 mm to 0.3 mm. To further illustrate, for a given minimum bend diameter (ID) of 1 mm and a tape thickness 0.050 mm, two to twenty loops may result in an outer diameter (OD) of approximately 1.2 mm to 3 mm with a combined coil thickness of 0.1 mm to 1.0 mm. Accordingly, at 20 loops, this embodiment may allow for the input coil 320 to have an OD of approximately 1.6 mm to 3 mm and a total coil thickness of approximately 0.3 mm to 1.0 mm. It should be understood that other combinations of number of loops, minimum bend diameters, and tape thickness' are contemplated, particularly as performance and manufacturing requirements may vary.

Figure 18:
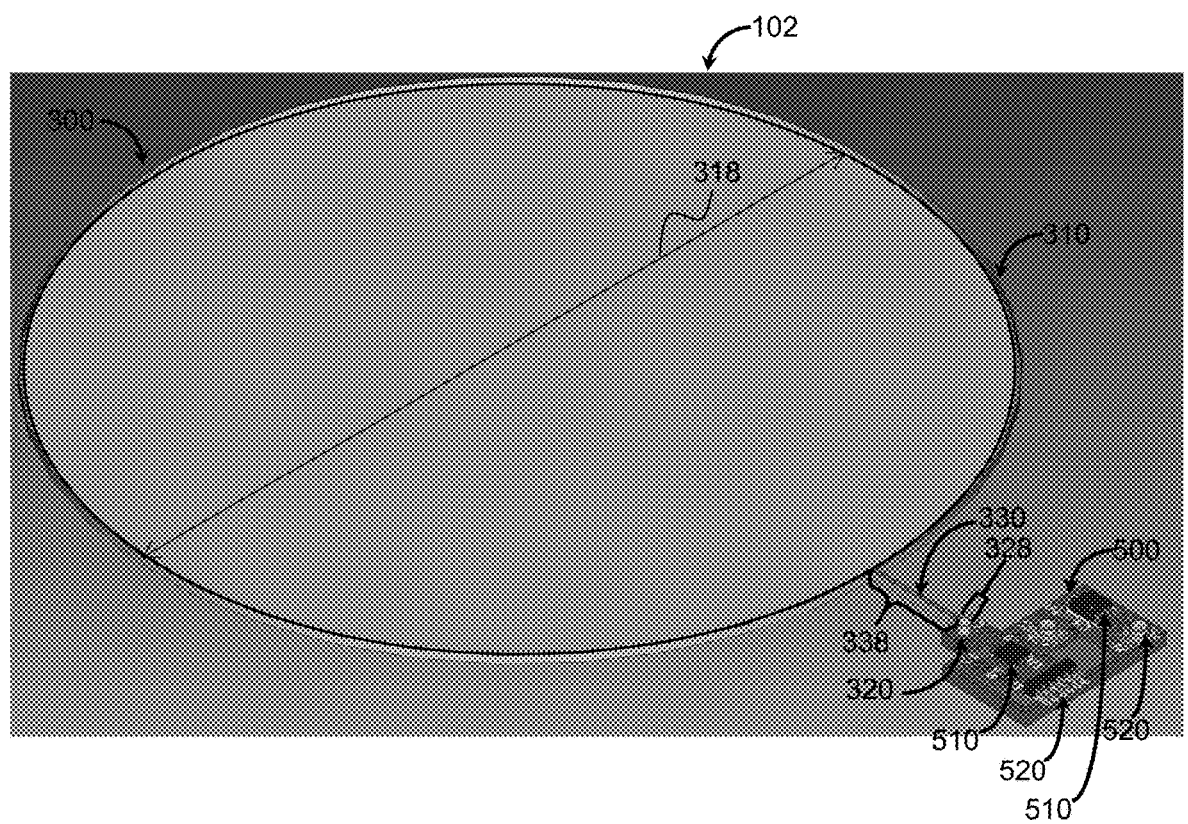
FIG. 18 is perspective view of an exemplary electronic device incorporating a magnetic flux pickup and a SQUID, according to one embodiment of the present disclosure.

FIG. 18 is perspective view of an exemplary electronic device incorporating a magnetic flux pickup and a SQUID, according to one embodiment of the present disclosure. Here, an electronic device 102 is integrated with a circuit board 500 configured for a specific application. The circuit board 500 is very broadly defined and may generally include one or more processors 510 and one or more input/outputs 520. As above, the electronic device 102 may include the first electronic device terminal 110, the second electronic device terminal 120, the SQUID 150, the SQUID coupling loop 130, and the magnetic flux pickup 300, where the magnetic flux pickup 300 may include the magnetic flux pickup loop 310, the input coil 320, and the pair of extension arms 330.

According to one exemplary embodiment, and conveniently using commonly recognized characteristic dimensions (e.g., diameters and lengths), the magnetic flux pickup loop 310 may be orders of magnitude greater than the input coil 320 and the SQUID coupling loop 130, which may be orders of magnitude greater than the SQUID 150 (particularly as a nanoSQUID). Additionally, the magnetic flux pickup loop 310 may be orders of magnitude greater, on the order of, or even orders of magnitude smaller than the pair of extension arms 330. Beneficially, this qualitative sizing may provide for improved sensing, as well as remote cooling.

For example, the SQUID coupling loop 130 may have its coupling loop diameter 139 less than 1 millimeter. The input coil 320 may similarly have its outer, average 328, or inner diameter less than 1 millimeter. The magnetic flux pickup loop 310 may have its loop diameter 318 at least 50 millimeters. Further, the magnetic flux pickup loop 310 may have its loop diameter 318 less than 150 millimeters. According to one embodiment, the pair of extension arms 330 may be at least 10 times longer than the coil diameter input coil 320 of the input coil 320. For example, here the pair of extension arms 330 may have an arm length 338 at least 10 millimeters.

Figure 19:
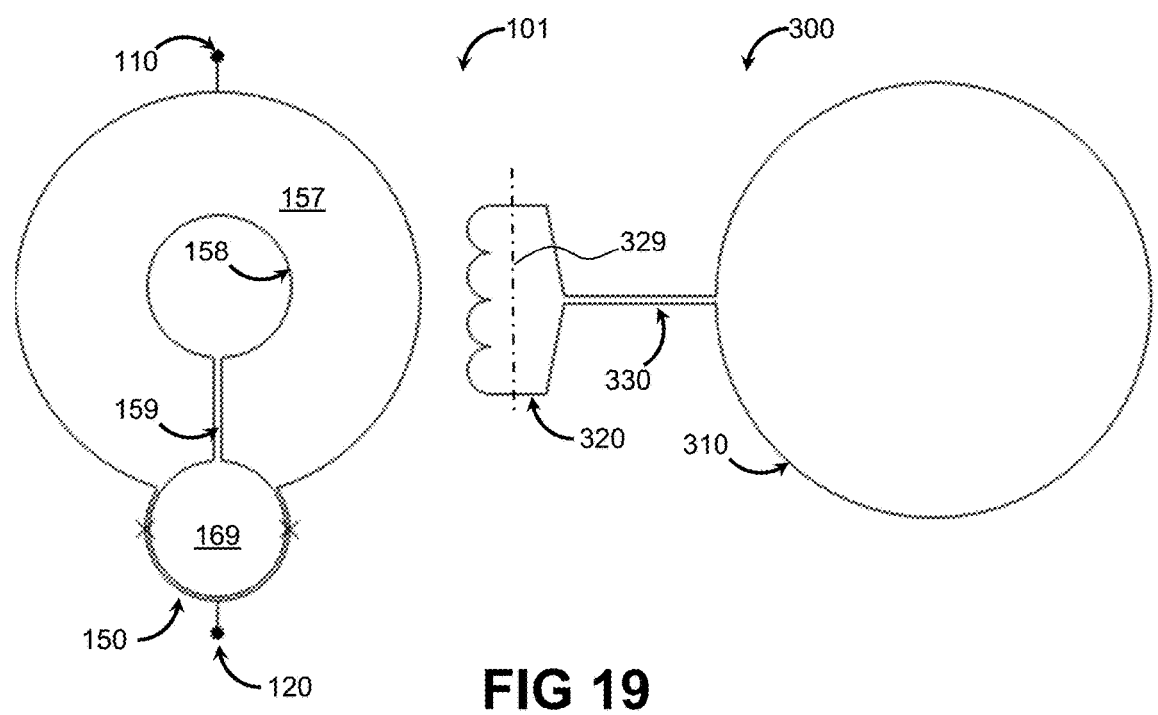
FIG. 19 is a schematic diagram of a magnetic flux pickup coupled to a SQUID, according to another embodiment of the present disclosure. LENZ LENS

FIG. 19 is a schematic diagram of a magnetic flux pickup coupled to a SQUID, according to another embodiment of the present disclosure. As above, the electronic device 101 may include the first electronic device terminal 110, the second electronic device terminal 120, the SQUID 150, and the magnetic flux pickup 300, where the magnetic flux pickup 300 may include the magnetic flux pickup loop 310, the input coil 320, and the pair of extension arms 330. In this embodiment, the SQUID 150 is a "washer SQUID" there is no abovementioned SQUID coupling loop.

Accordingly and as shown the SQUID 150 may be configured as a washer SQUID or otherwise integrate a "washer" type of structure. The washer type structure may be used to geometrically match the SQUID 150 to the input coil 320 without increasing the SQUID's inductance excessively. When the input coil 320 rests on top (or below) of the washer structure, it will couple flux into the washer's center and into the SQUID 150.

The "washer" structure generally includes a large superconducting washer exterior 157, with a hollow center 158 and a slot 159, where the washer exterior 157 makes up a part of the SQUID 150. The slot 159, of the washer structure proceeds radially outward from the hollow center 158 down to the aperture 169 of the SQUID 150, and generally prevents completing the circuit of the abovementioned SQUID coupling loop. The size of the hollow center 158 (here characterized as an inner diameter of the washer shape) may be on order of the aperture 169 of the SQUID 150 (here characterized as an inner diameter of between the Josephson Junctions), for example, up to 10 times its size.

The size of the hollow center 158 (again characterized by the inner diameter of the washer shape) is significantly less than the size of the washer exterior 157 (here characterized as an outer diameter of the washer shape), which keeps the inductance down. For example the outer diameter (OD) of the washer shape may be 10-1000 times larger, diametrically, than the inner diameter (ID) of the washer shape.

It should be understood that the SQUID 150 is illustrated in an exemplary manner, and may not be dimensionally correct for all contemplated embodiments. Further, while the washer structure may be shaped as circle, as shown, and made of a high temperature superconductor, washer SQUIDs may have a washer structure shaped as a square or rectangle, for example, when made of a low temperature superconductor. Accordingly, the washer SQUID may be arranged as a low temperature superconducting washer SQUID.

Figure 20:
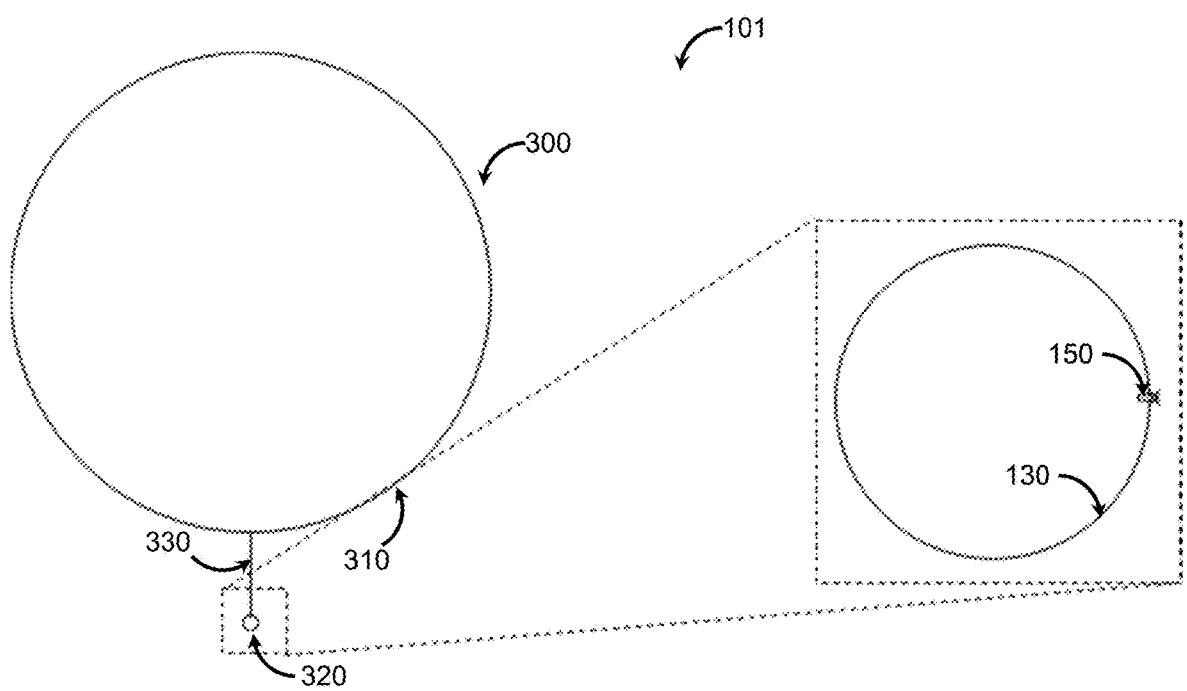
FIG. 20 is a schematic diagram of a magnetic flux pickup coupled to a SQUID, according to another embodiment of the present disclosure.
Figure 21:
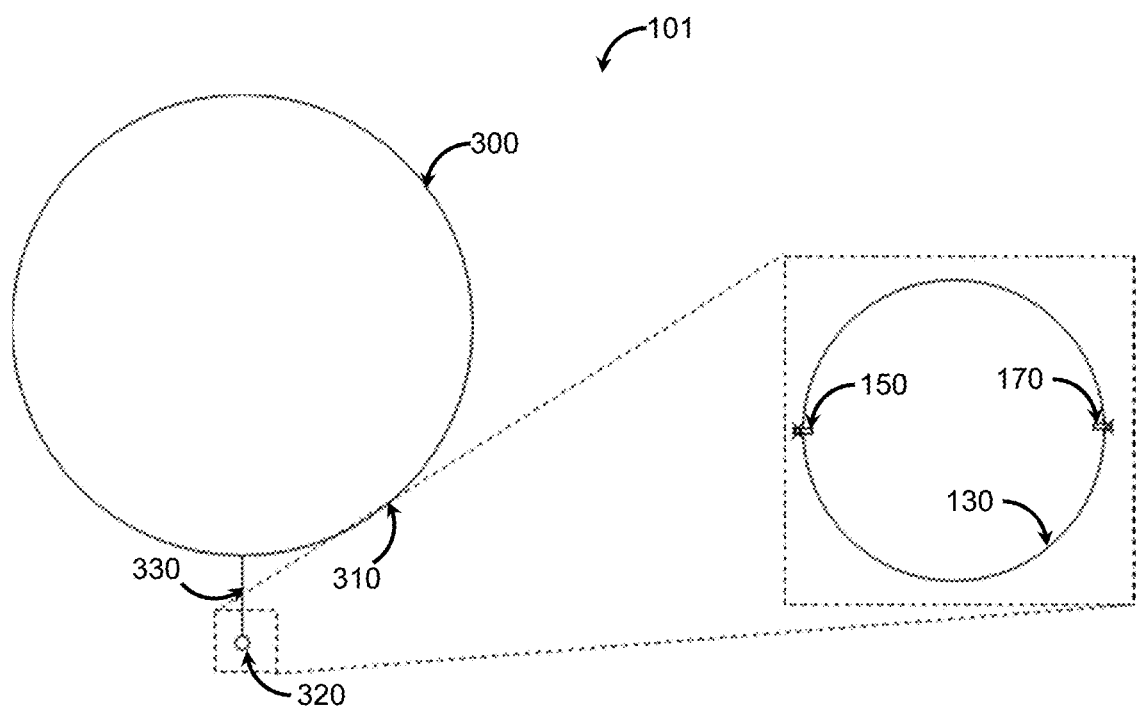
FIG. 21 is a schematic diagram of an exemplary electronic device incorporating a magnetic flux pickup and a plurality of SQUIDs, according to one embodiment of the present disclosure.
Figure 22:
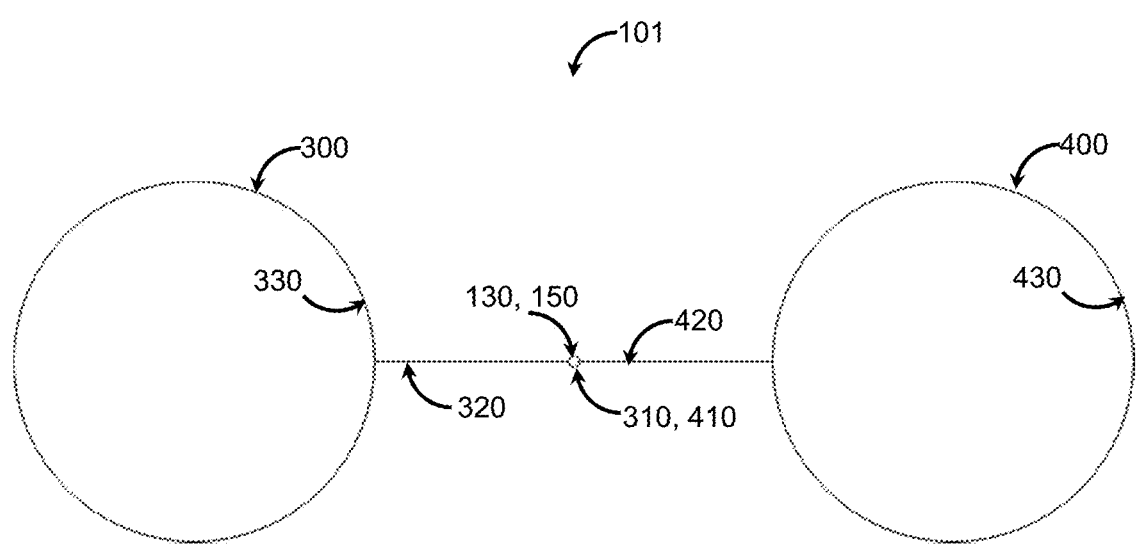
FIG. 22 is a schematic diagram of a plurality of input coils coupled to a SQUID, according to another embodiment of the present disclosure.

FIG. 20 is a schematic diagram of a magnetic flux pickup coupled to a SQUID, according to one embodiment of the present disclosure, and as discussed above. FIG. 21 is a schematic diagram of an exemplary electronic device incorporating a magnetic flux pickup and a plurality of SQUIDs, according to one embodiment of the present disclosure. FIG. 22 is a schematic diagram of a plurality of input coils coupled to a SQUID, according to yet another embodiment of the present disclosure. Here, various exemplary configurations are shown as representative of some of the variations disclosed herein. As above, the electronic device 101 may generally include the SQUID 150, the SQUID coupling loop 130, and the magnetic flux pickup 300, where the magnetic flux pickup 300 may include the magnetic flux pickup loop 310, the input coil 320, and the pair of extension arms 330.

Referring to FIG. 20, according to one embodiment, the electronic device 101 may include a plurality of first SQUIDs 150 coupled in series (see ref., FIG. 7). In some instances the plurality of first SQUIDs 150 may be identical, and in others they may vary from one another (e.g., where different flux levels are to be measured).

Referring to FIG. 21, according to another embodiment, the electronic device 101 may include the first SQUID 150 and a second SQUID 170 in a parallel configuration, as discussed above (see ref., FIG. 6). As shown, both the first SQUID 150 and the second SQUID 170 may be configured to inductively couple to the same input coil 320. According to one embodiment, the electronic device 101 may include a plurality of the first SQUIDs 150 coupled in series (see ref., FIG. 7) and/or a plurality of the second SQUIDs 150 coupled in series, thus forming a series-parallel configuration. In some instances the plurality of first/second SQUIDs 150, 170 may be identical, and in others they may vary from one another (e.g., where different flux levels are to be measured).

Referring to FIG. 22, according to yet another embodiment, the electronic device 101 may include a second the magnetic flux pickup 400 that is identical to the first magnetic flux pickup 300 described above. Similarly, the second the magnetic flux pickup 400 may include a second magnetic flux pickup loop 410, a second input coil 420, and a second pair of extension arms 430, also as described above. According to one embodiment, the first magnetic flux pickup loop 310 and the second magnetic flux pickup loop 410 may be positioned on opposing sides of the SQUID coupling loop 130 or SQUID 150. Alternately, the first magnetic flux pickup loop 310 and the second magnetic flux pickup loop 410 may be a single element or otherwise be shared.

As shown, both the first magnetic flux pickup 300 and the second magnetic flux pickup 400 may be configured to inductively couple to the same SQUID coupling loop 130 or SQUID 150. Accordingly, here, a single SQUID coupling loop 130 and SQUID 150‖ are located underneath a shared first/second magnetic flux pickup loop 310, 410. According to one embodiment, the electronic device 101 may include additional magnetic flux pickups.

In some embodiments, the SQUID coupling loop 130 may include one or more SQUIDs 150, 170, in series and/or parallel, which may be identical or vary. Further, here, and in the preceding exemplary embodiments, the electronic device 101 may include any additional element, feature, and/or variation discussed herein, for example, the electrical barrier 192 for mitigating parasitic SQUIDs, the magnetic flux shield 194 (e.g., Lenz lens) focusing magnetic flux into the coupling loop and/or shielding flux from entering the parasitic SQUIDs 190 and the Josephson Junctions of the SQUIDs 150, 170, etc. Further, the electronic device 102 may include or otherwise be coupled to the circuit board 500 or other nanoSQUID electronics 200, which may include a Flux Locked Loop (FLL) useful for measuring a dynamic range of flux fields or applied as a Superconducting Quantum Interference Filter (SQIF), as well as any appropriate control electronics. Beneficially, this embodiment, may be useful as a gradiometer, where immersion of both the first magnetic flux pickup 300 and the second the magnetic flux pickup 400 in the same flux field will result in a mutual cancellation, and only differences or gradient in the field will be "picked up".

Figure 23:
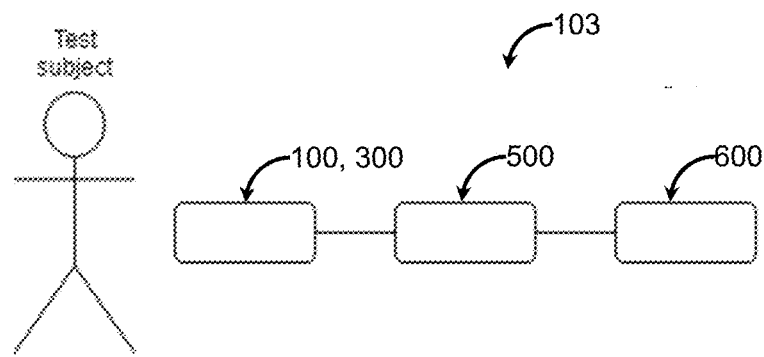
FIG. 23 is a schematic diagram of an exemplary electronic device incorporating a magnetic flux pickup and a SQUID, configured for biomedical imaging, according to one embodiment of the present disclosure.
Figure 24:
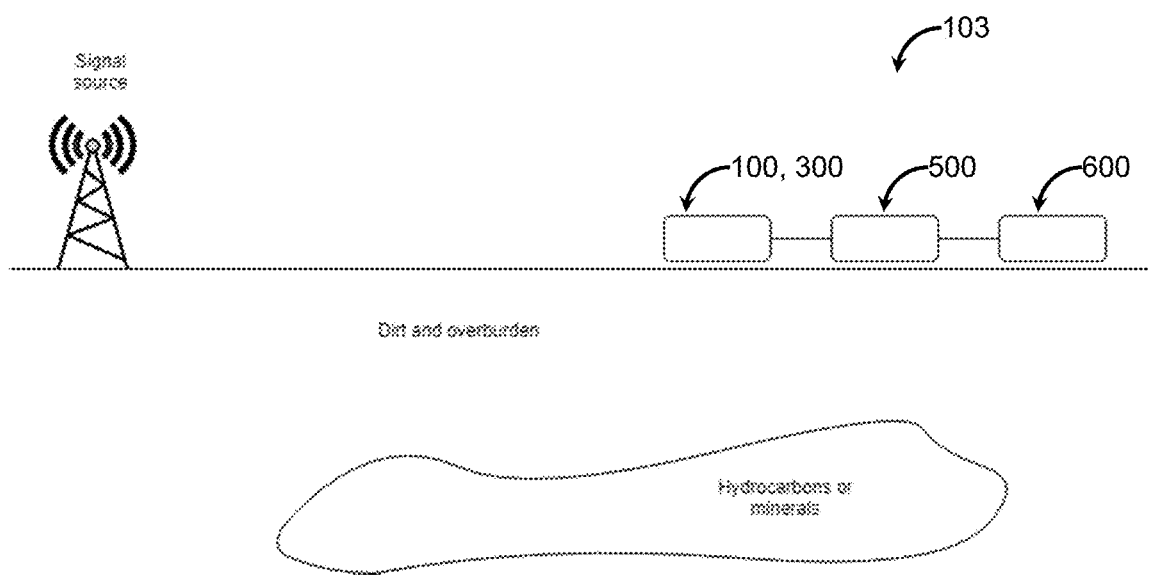
FIG. 24 is a schematic diagram of an exemplary electronic device incorporating a magnetic flux pickup and a SQUID, configured for geophysical imaging, according to one embodiment of the present disclosure.

FIG. 23 is a schematic diagram of an application specific electronic device for sensing a sensed property incorporating a magnetic flux pickup and a SQUID, configured for biomedical imaging, according to one embodiment of the present disclosure. FIG. 24 is a schematic diagram of an exemplary electronic device incorporating a magnetic flux pickup and a SQUID, configured for geophysical imaging, according to one embodiment of the present disclosure. As shown, an application specific electronic device 103 for sensing a sensed property may include the electronic device 100 for sensing magnetic fields, the magnetic flux pickup 300, and the circuit board 500 configured for the specific application, as described above.

Further, the application specific electronic device 103 may include or otherwise incorporate sensing support infrastructure 600. The sensing support infrastructure 600 is very broadly defined and may generally include one of more of data processing, visualization, storage, and environmental controls, as well as other components associated with detecting, measuring, and using the sensed property. For example, the sensing support infrastructure 600 may include any appropriate components useful for applying sensed magnetic fields to biomedical imaging, geophysical imaging, communications, and the like.

To illustrate, the sensing support infrastructure 600 may include a cryogenic system configured to cool the SQUID below its critical temperature, a means to reduce magnetic fields from secondary sources such as magnetic shielding, an application specific signal processor configured to read and interpret voltages between the first terminal 110 and the second terminal 120 (or their equivalents) as a magnetic field strength, and a data processor and user interface configured to interpret the magnetic field strength according to the sensed property, and to the communicate the sensed property to a user, just to name a few.

According to one embodiment, the application specific electronic device 103 may be configured to increase the sensitivity and voltage response of the device and/or for dynamic sensing. In general, as discussed above, the application specific electronic device 103 may include or otherwise incorporate a plurality of SQUIDs (e.g., nanoSQUIDs) electrically coupled in series and/or in parallel, each SQUID having a different sensitivity with respect to the input signal. The plurality of SQUIDs may be patterned on the edge of the coupling loop in a series and/or parallel configuration and in conjunction with the magnetic flux pickup 300.

The application specific electronic device 103 may further include SQUID electronics electrically coupled to each of the plurality of SQUIDs, the SQUID electronics configured to provide Flux Locked Loop (FLL) feedback to the SQUIDs, and a means to reset each SQUID's FLL (e.g., a SQUID FLL reset or other electronic switching configured to disconnect the FLL's input or output/feedback). In this way, application specific electronic device 103 may be used in a SQUID cascade, which utilizes two or more independent devices with different sensitivities to achieve an extended dynamic range.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. The foregoing method descriptions and steps are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods.

The above description of the various embodiments is provided to enable a person of ordinary skill in the art to make or use the subject matter of the disclosure. Various modifications to the embodiments will be readily apparent to those skilled in the art, and the generic principles defined herein may be applied to other variations without departing from the spirit or the scope of this disclosure. Thus, it is to be understood that the disclosure is not intended to be limited to the examples and designs described herein, which merely represent a presently preferred implementation of the disclosure, but that the disclosure is to be accorded the widest scope consistent with the principles and novel features disclosed herein. It is to be further understood that the scope of the present disclosure fully encompasses other embodiments that may become obvious to those skilled in the art.

The invention claimed is:

1. An electronic device for sensing magnetic fields, the electronic device comprising:
a first electronic device terminal;
a second electronic device terminal;
a first Superconducting Quantum Interference Device (SQUID) including a first superconducting trace extending between two first opposing ends, a second superconducting trace extending between two second opposing ends, and a first pair of Josephson Junctions electrically coupled in parallel between each of the first superconducting trace and the second superconducting trace at the first opposing ends and second opposing ends of the first superconducting trace and the second superconducting trace, respectively, the first SQUID electrically coupled in series between the first terminal via the first superconducting trace, and the second terminal via the second superconducting trace;
a SQUID coupling loop made of a first superconducting material shaped into a closed loop about a coupling center axis, the SQUID coupling loop characterized by a coupling loop diameter defined as an average diametrical distance between opposing sides of the closed loop, the SQUID coupling loop integrated with the second superconducting trace such that the second superconducting trace forms a first segment of the superconducting loop, the SQUID coupling loop electrically coupled in series between the first terminal via the second superconducting trace and the second terminal;
a magnetic flux pickup including
a magnetic flux pickup loop having a pickup loop center axis, the magnetic flux pickup loop including a first pickup end, a second pickup end, and an open loop, said open loop extending between the first pickup end and the second pickup end and circumscribing at least 350 degrees about the pickup loop center axis, the pickup loop made of a second superconducting material, the open loop characterized by a loop diameter defined as an average diametrical distance between opposing sides of the open loop, and
an input coil having an input coil center axis, the input coil including a first coil terminal end and a second coil terminal end, and a coil of at least one loop, said coil extending between the first coil terminal end and the second coil terminal end and circumscribing at least 350 degrees about both the input coil center axis of the input coil and the coupling center axis of the SQUID coupling loop, the input coil made of a superconducting tape having a tape width and tape thickness, said tape thickness of the superconducting tape being less than 0.050 millimeter, the input coil characterized by a coil diameter defined as an average diametrical distance between opposing sides of the coil, the first terminal coil end electrically coupled to the first pickup end of the magnetic flux pickup loop, the second coil terminal end electrically coupled to the second pickup end of the magnetic flux pickup loop.

2. The electronic device of claim 1, wherein the loop diameter of the magnetic flux pickup loop is between 25 millimeters and 150 millimeters; and
wherein the coil of the input coil has between 2 and 20 loops, the coil diameter of the input coil is less than 5 millimeters, and the high temperature superconducting tape of the input coil has a tape width and tape thickness, said tape width being at least 0.5 millimeter.

3. The electronic device of claim 1, wherein the input coil and the SQUID coupling loop are sized and dimensioned such that the coil diameter and the coupling loop diameter are within 25% of each other.

4. The electronic device of claim 1, further comprising a pair of extension arms made of a third superconducting material, said pair of extension arms extending between and electrically coupling the first terminal coil end of the input coil to the first pickup end of the magnetic flux pickup loop, and the second terminal coil end of the input coil to the second pickup end of the magnetic flux pickup loop, respectively; and
wherein each of the pair of extension arms are at least 10 times longer than the coil diameter of the input coil.

5. The electronic device of claim 1, wherein the first superconducting trace has a first trace length as measured between one junction end of each of the first pair of Josephson Junctions, said first trace length being less than 999 nm, and the second superconducting trace has a second trace length as measured between an other junction end of each of the first pair of Josephson Junctions, said second trace length being at least twice the first trace length.

6. The electronic device of claim 1, further comprising a superconducting circuit configured to shield the first SQUID, the SQUID coupling loop, and the input coil from magnetic flux that does not originate from the input coil.

7. The electronic device of claim 1, further comprising a second SQUID including a third superconducting trace extending between two third opposing ends, a fourth superconducting trace extending between two fourth opposing ends, and a second pair of Josephson Junctions electrically coupled in parallel between each of the third superconducting trace and the fourth superconducting trace at the third opposing ends and fourth opposing ends of the third superconducting trace and the fourth superconducting trace, respectively, the second SQUID electrically coupled in series between the second terminal via the third superconducting trace, and the first terminal via the fourth superconducting trace; and
wherein the SQUID coupling loop is electrically coupled in series between the second terminal via the third superconducting trace.

8. The electronic device of claim 7, wherein the first SQUID and the second SQUID each include a plurality of identical SQUIDs electrically coupled in parallel.

9. An application specific electronic device for sensing a sensed property, the application specific electronic device comprising:
a first electronic device terminal;
a second electronic device terminal;
a Superconducting Quantum Interference Device (SQUID) including a first superconducting trace extending between two first opposing ends, a second superconducting trace extending between two second opposing ends, and a first pair of Josephson Junctions electrically coupled in parallel between each of the first superconducting trace and the second superconducting trace at the first opposing ends and second opposing ends of the first superconducting trace and the second superconducting trace, respectively, the SQUID electrically coupled in series between the first terminal via the first superconducting trace, and the second terminal via the second superconducting trace;
a SQUID coupling loop made of a first superconducting material shaped into a closed loop about a coupling center axis, the SQUID coupling loop characterized by a coupling loop diameter defined as an average diametrical distance between opposing sides of the closed loop, the SQUID coupling loop integrated with the second superconducting trace such that the second superconducting trace forms a first segment of the superconducting loop, the SQUID coupling loop electrically coupled in series between the first terminal via the second superconducting trace and the second terminal;
a magnetic flux pickup including
a magnetic flux pickup loop having a pickup loop center axis, the magnetic flux pickup loop including a first pickup end, a second pickup end, and an open loop, said open loop extending between the first pickup end and the second pickup end and circumscribing at least 350 degrees about the pickup loop center axis, the pickup loop made of a second superconducting material, the open loop characterized by a loop diameter defined as an average diametrical distance between opposing sides of the open loop, and
an input coil having an input coil center axis, the input coil including a first coil terminal end and a second coil terminal end, and a coil of at least one loop, said coil extending between the first coil terminal end and the second coil terminal end and circumscribing at least 350 degrees about both the input coil center axis of the input coil and the coupling center axis of the SQUID coupling loop, the input coil made of a superconducting tape having a tape width and tape thickness, said tape thickness of the superconducting tape being less than 0.050 millimeter, the input coil characterized by a coil diameter defined as an average diametrical distance between opposing sides of the coil, the first terminal coil end electrically coupled to the first pickup end of the magnetic flux pickup loop, the second coil terminal end electrically coupled to the second pickup end of the magnetic flux pickup loop.
a cryogenic system configured to cool the SQUID below its critical temperature;
a means to reduce magnetic fields from secondary sources;
an application specific signal processor configured to read and interpret voltages between the first terminal and the second terminal as a magnetic field strength; and
a data processor and user interface configured to interpret the magnetic field strength according to the sensed property, and to communicate the sensed property to a user.

10. The application specific electronic device of claim 9, wherein the SQUID includes a plurality of SQUIDs electrically coupled in parallel, each SQUID having a different sensitivity with respect to the input signal, the application specific electronic device further comprising:
a connection for an input signal;
SQUID electronics electrically coupled to each of the plurality of SQUIDs, the SQUID electronics configured to provide Flux Locked Loop (FLL) feedback to the SQUIDs;
a means to reset each SQUID's FLL.

11. The application specific electronic device of claim 9, wherein the sensed property is directed toward geophysical sensing or biomedical imaging.

* * * * *